US006906241B2

(12) United States Patent
Davis et al.

(10) Patent No.: US 6,906,241 B2
(45) Date of Patent: Jun. 14, 2005

(54) ENDOGLUCANASE GENE PROMOTER UPREGULATED BY NEMATODES

(75) Inventors: Eric L. Davis, Raleigh, NC (US); Melissa Goellner, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/970,367

(22) Filed: Oct. 2, 2001

(65) Prior Publication Data

US 2003/0106092 A1 Jun. 5, 2003

(51) Int. Cl.[7] .................. C12N 15/09; C12N 15/82; A01H 5/00; A01H 5/10
(52) U.S. Cl. .................. 800/287; 800/278; 800/298; 800/301; 800/320; 800/317; 800/279; 435/320.1; 435/468; 435/419; 435/430.1; 536/23.4
(58) Field of Search ................. 800/279, 278, 800/298, 301, 320, 317, 287, 295; 435/320.1, 468, 419, 430.1; 536/23.4, 23.2, 23.6, 24.1

(56) References Cited

U.S. PATENT DOCUMENTS

| 5,459,252 A | 10/1995 | Conkling et al. |
| 5,589,622 A | 12/1996 | Gurr et al. |
| 5,750,386 A | 5/1998 | Conkling et al. |
| 5,837,876 A | 11/1998 | Conkling et al. |

OTHER PUBLICATIONS

Keller et al . The Plant Cell, vol. 3, pp. 1051–1061, 1991.*
Kim et al. Plant Molecular Biology, vol. 24, pp. 105–117, 1994.*

* cited by examiner

Primary Examiner—Amy J. Nelson
Assistant Examiner—Medina A. Ibrahim
(74) Attorney, Agent, or Firm—Myers Bigel Sibley & Sajovec, P.A.

(57) ABSTRACT

The present invention provides a nucleic acid construct comprising a cyst and root knot nematode responsive promoter, preferably the *Nicotiana* Ntcel7 promoter or promoters that hybridize thereto, operatively associated with a heterologous nucleic acid segment that encodes a product disruptive of nematode attack. Plants and plant cells using the same and methods of use thereof are also disclosed.

23 Claims, 6 Drawing Sheets

```
Ntcel7 ----------MAF.RVEVSVC.IILFSSFFFSLGTAQGVFNYR 31 (SEQ ID NO:4)
Ntcel2 MARKNCGFPAGFPSFPLSLA.LIFFLPVNPLRHCSAGGHDYR 41 (SEQ ID NO:2)
Ntcel8 -------MMKSFVMMFCSMTPLLLIIGLLPNLAFASS.HNYG 34 (SEQ ID NO:6)

Ntcel7 EAIEKSILFFFGQRSGKLPHNQRVSWRGSSGLSDGSLAKVDL  73 (SEQ ID NO:4)
Ntcel2 DAIRKSILFFFGQRSGKLPPDQRIKWRKDSALMDGASAGVDL  83 (SEQ ID NO:2)
Ntcel8 EAISKSFLFYEAQRSGYLPHDQRVQWRGNSGLLDGKASGVDL  76 (SEQ ID NO:6)

Ntcel7 TGGYYDAGDNVKFNFPMAYIITLLSWNTLEYGKRMGP...QLQ 113 (SEQ ID NO:4)
Ntcel2 TGGYYDAGDNVKFVFPMAFIITLLSWSIIDFKRNIGR...ELG 123 (SEQ ID NO:2)
Ntcel8 VGGYYDAGDNVKFGLPMAFIVMMMSWSIIEYGKQMGESGELS 118 (SEQ ID NO:6)

Ntcel7 NARAAIRWATDYLLKCANAAPNKLFVGVGDPNSDHKCWERPE 155 (SEQ ID NO:4)
Ntcel2 NAVKAVKWATDFLLK.ATAKEGVIYVQVGDAFSDHSCWERPE 164 (SEQ ID NO:2)
Ntcel8 NAIDAVKWGTDYLLK.AHPEPNVLYGEVGDGTTDHYCWQRPE 159 (SEQ ID NO:6)

Ntcel7 DMDIVRSVYYVSPSSPGSDVAGEMAAAIAAASLVFRTVDPVY 197 (SEQ ID NO:4)
Ntcel2 DMDILRTVYKIDQNHPGSDVAGEIAASLAAASIVFRSLDSSY 206 (SEQ ID NO:2)
Ntcel8 DMTISRAAYRIDPSRPGSDLAGETAAAMAAASIVFRNSNPAY 201 (SEQ ID NO:6)

Ntcel7 SKKLLGNAVKVFRFAVQYRGSYSDSLGSAACPFYCSYSGYKD 239 (SEQ ID NO:4)
Ntcel2 SGLLLDRAVKVFEFANRHRGAYSSSLHSAVCPFYCDFDGYQD 248 (SEQ ID NO:2)
Ntcel8 AKELLTHAYQLFEFADKYRGKYDSSI.TVAQKYYRSVSGYAD 242 (SEQ ID NO:6)

Ntcel7 ELYWGAAWLLRATNDISYLNFI..N..TL.GANDVPDLFSWD 276 (SEQ ID NO:4)
Ntcel2 EILWGAAWIHKATRRRQYREYIVKNEVVL.RAGDTINEFGWD 289 (SEQ ID NO:2)
Ntcel8 ELLWAAAWLYKASNKEYYYLNYLGENGDALGGTGWSMTEFGWD 284 (SEQ ID NO:6)

Ntcel7 NKYAGAHVLMARRSVVGN....DKRFDPFRQQAEDFVCKILP 314 (SEQ ID NO:4)
Ntcel2 NKHAGINVLISKEVLMGR....APDLKSFQVNADAFICSILP 327 (SEQ ID NO:2)
Ntcel8 VKYAGVQTLAAKFLMQGNAGNHAPVFEKYQEKAENFMCACL. 325 (SEQ ID NO:6)

Ntcel7 NSPYTSTQYTKGGLIYKLTEENLQYVTSITSLLTTYAKYMAS 356 (SEQ ID NO:4)
Ntcel2 GISHPQVQYSPGGLIVKPGVCNMQFVTSLSFLLAYSNYLSH 369 (SEQ ID NO:2)
Ntcel8 GKGNQNIHKSPGGLIFRQRWNNMQFVTSASFLATVYSDYLAS 367 (SEQ ID NO:6)

Ntcel7 KKHTFNCGSLLVTEKTIRILAKRQVDYILGNNPMKMSYMVGY 398 (SEQ ID NO:4)
Ntcel2 ANHAVPCGSISATPALLKHIAKRQVDYILGDNHQRMSYMVGY 411 (SEQ ID NO:2)
Ntcel8 ARKSLKCSSGTVLPSELLSFAKSQVDYILGDNHRATSYMVGY 409 (SEQ ID NO:6)

Ntcel7 GTNYPRRVHHRGSSLPSMAMHPQSFGCDGGFQPYYYTANANE 440 (SEQ ID NO:4)
Ntcel2 GPRYPLRIHHRGSSLPSVAAHPARIGCKGG.SNYFLSPNPNE 452 (SEQ ID NO:2)
Ntcel8 GNNYPRQVHHRGSSIVSVKKDESFVSCRGGYATWFSRKASDE 451 (SEQ ID NO:6)

Ntcel7 NIFVGAIVGGPNQNDFFPDERTDYSHSEPATYINAAIVGPLA 482 (SEQ ID NO:4)
Ntcel2 NRIIGAVVGGPNITDSFPDARPFFQESEPITYVNAPLVGLLA 494 (SEQ ID NO:2)
Ntcel8 NLIAGAIVGGEDAYDNFADQRDNYEQTEPATYNNAPLIGVLA 493 (SEQ ID NO:6)

Ntcel7 YFDSSER------------------------------------ 489 (SEQ ID NO:4)
Ntcel2 YFSAHT------------------------------------- 500 (SEQ ID NO:2)
Ntcel8 RLHGGQSKYSQLLPVAIPQPKPDPEQKVTPAPASSTADITIE 535 (SEQ ID NO:6)

Ntcel7 ------------------------------------
Ntcel2 ------------------------------------
Ntcel8 QKETASWVPKGKTYYRYSVIVTNKSAMTMKNLKLSIYQLYGS 577 (SEQ ID NO:6)

Ntcel7 ------------------------------------
Ntcel2 ------------------------------------
Ntcel8 LWGLSKYGDSYVFPAWLNSLPAGKTLEFVYVHSASPATVSIS 619 (SEQ ID NO:6)

Ntcel7 -----
Ntcel2 -----
Ntcel8 SYTLV  624 (SEQ ID NO:6)
```

ENDOGLUCANASE GENE PROMOTER UPREGULATED BY NEMATODES

FIELD OF THE INVENTION

This invention relates to tissue-specific gene promoters, and particularly relates to a promoter which is responsive to the cyst and root knot nematodes.

BACKGROUND OF THE INVENTION

A promoter is a DNA sequence which flanks a transcribed gene, and to which RNA polymerase must bind if it is to transcribe the flanking gene into messenger RNA. A promoter may consist of a number of different regulatory elements which affect a structural gene operationally associated with the promoter in different ways. For example, a regulatory gene may enhance or repress expression of an associated structural gene, subject that gene to developmental regulation, or contribute to the tissue-specific regulation of that gene. Modifications to promoters can make possible optional patterns of gene expression, using recombinant DNA procedures. See, e.g., Old and Primrose, Principles of Gene Manipulation (4th Ed., 1989).

U.S. Pat. No. 5,459,252 to Conkling and Yamamoto describes a root specific promoter designated RB7, which was identified in tobacco. U.S. Pat. No. 5,837,876 to Conkling et al. describes a root cortex specific gene promoter designated the RD2 promoter, which was also identified in tobacco.

Rather than use a promoter that is constitutively active, it is desirable to have promoters that are responsive to particular stimuli. In particular, if a promoter is responsive to a particular pathogen, then that promoter could be used to impart selective disease resistance to that pathogen through expression of a transgene that disrupts that pathogen.

U.S. Pat. No. 5,750,386 to Conkling, Opperman and Taylor describes pathogen resistant transgenic plants in which a nematode-responsive element is operatively associated with a nucleotide of interest (in this case, a gene encoding a product toxic to plant cells). One nematode responsive element was a deletion fragment of the RB7 root specific promoter described above.

U.S. Pat. No. 5,589,622 to Gurr et al. suggests nematode resistant transgenic plants in which cells of the plant contain a heterologous construct comprising a nematode responsive promoter operatively associated with a product disruptive of nematode attack. However, the DNAs disclosed by Gurr et al. as nematode responsive promoters do not appear to represent such promoters, and instead appear to represent extraneous or irrelevant DNA.

To impart useful traits to plants by the expression of foreign genes using genetic engineering techniques, a variety of pathogen-responsive promoters will be required to allow traits to be expressed selectively, in the appropriate plant tissues, and at the appropriate times. Accordingly, there is a continued need for pathogen responsive elements that operate in plant cells.

SUMMARY OF THE INVENTION

The present invention is based on the discovery that the endo-1,4-β-glucanases, Ntcel2 (SEQ ID NO:1), Ntcel7 (SEQ ID NO:3), and Ntcel8 (SEQ ID NO:5), of *Nicotiana tabacum* are upregulated in cyst and root-knot nematode feeding cells (i.e., giant cells). Plant parasitic nematodes cause approximately 100 billion dollars annually in crop loses worldwide. The root knot nematode has a host range of over 2000 plant species, and is one of the most damaging nematodes.

Accordingly, a first aspect of the present invention is an isolated nucleic acid, particularly DNA, molecule which directs cyst and/or root knot nematode responsive transcription of a downstream heterologous nucleic acid/DNA segment in a plant cell (i. e., a promoter), and the use thereof in providing or imparting nematode resistance to plants and plant cells. Preferably the promoter is responsive to, or activates transcription in response to, both cyst and root knot nematodes.

A further aspect of the present invention is a construct comprising a promoter as described above and a heterologous nucleic acid/DNA segment (i. e., a DNA segment not naturally associated with that promoter) positioned downstream from, and operatively associated with, the promoter. The heterologous nucleic acid/DNA segment preferably encodes a product disruptive of nematode attack (i. e., a product that hinders or interferes with the ability of a nematode to feed upon a plant cell, or establish a feeding site in relationship to a plant cell, when that product is expressed in a plant cell).

Further aspects of the present invention are plant cells containing the above described constructs, methods of making transformed plants from such plant cells, the transformed plants comprising such transformed plant cells, and the use of the foregoing to impart resistance to root knot nematodes to plants.

BRIEF DESCRIPTION OF THE DRAWINGS

FIG. 2 shows an amino acid sequence comparison of Ntcel2 (SEQ ID NO:2), Ntcel7 (SEQ ID NO:4), and Ntcel8 (SEQ ID NO:6). Amino acid sequences were aligned using programs of the Wisconsin Package Version 10.0, Seqweb Version 1.1 (Genetics Computer Group, Madison, Wis.). Dots were introduced by the program to optimize the alignment. Black boxes depict identical amino acids among the three sequences. An arrowhead designates the putative secretion signal peptide cleavage sites of the proteins as determined by the SignalP V 1.1 program (Nielson, et al. (1997) *Protein Engin.* 10:1–6). Arrows designate two conserved amino acid domains used to amplify tobacco EGases from nematode-infected root tissue. An extra 124 amino acid sequence encoding a putative cellulose-binding domain at the C-terminus of Ntcel8 is underlined.

DETAILED DESCRIPTION OF THE PREFERRED EMBODIMENTS

Figure 1:
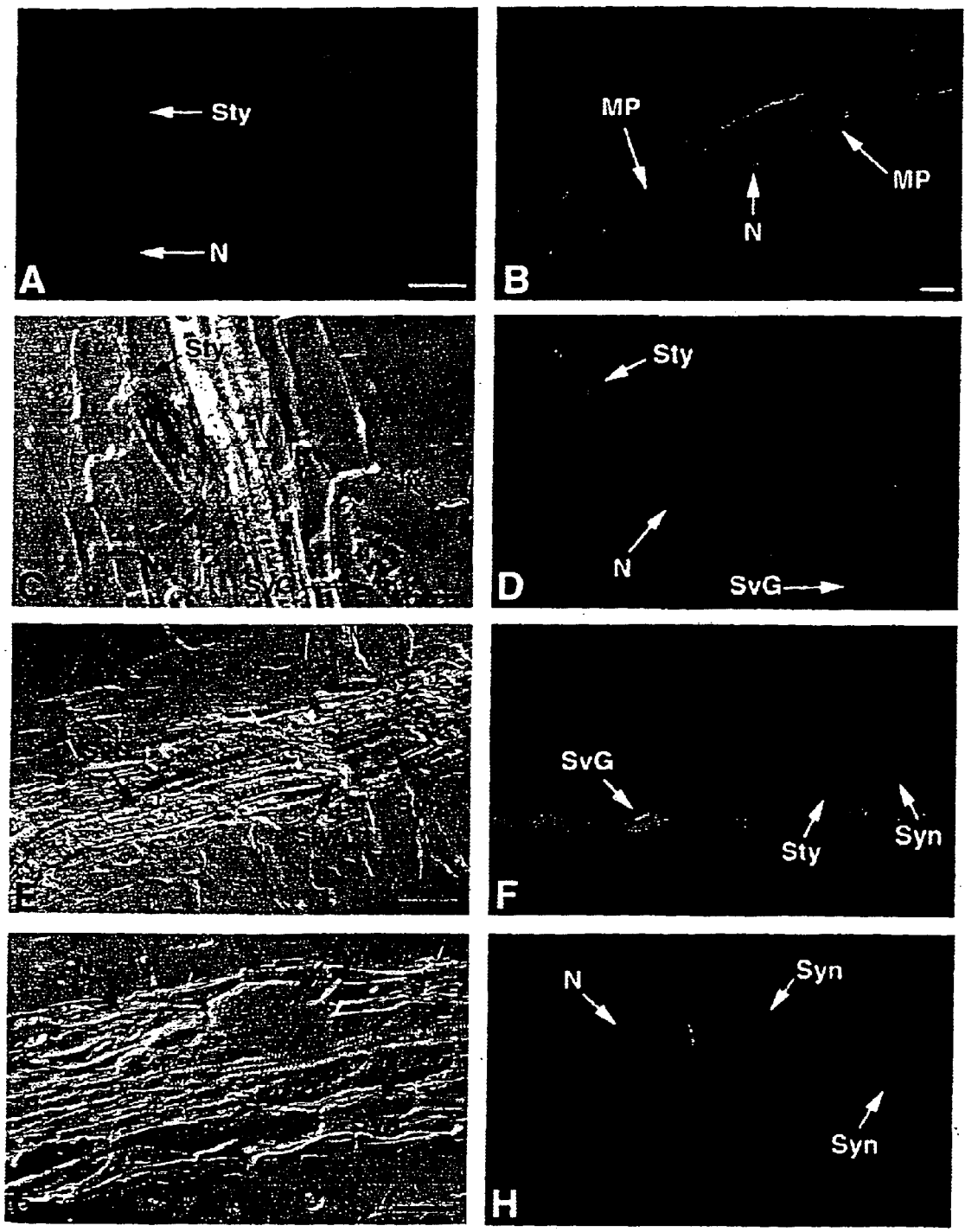
FIG. 1 shows the immunolocalization of EGases during parasitism of tobacco roots. (A) Longitudinal section through a tobacco root 24 h after inoculation with second-stage juveniles (J2) of *Globodera tabacum* (N) probed with mouse pre-immune serum. (B) Longitudinal section through a tobacco root 24h after inoculation with *G. tabacum* J2 and probed with GR-ENG-1 antiserum. Binding of the GR-ENG-1 antiserum (green fluorescence) is observed along the migratory path (MP) of multiple migratory juveniles within the root cortical tissue. An arrow points to a nematode tail (N). (C) Brightfield view of a longitudinal section through a tobacco root 24 h after inoculation with second-stage juveniles of *G. tabacum* (N) (D) Same section as C showing binding of GR-ENG-1 antiserum on the cell wall just outside the head of the nematode and within the nematode's subventral secretory gland cells (SvG). (E) Longitudinal section through a tobacco root containing a sedentary parasitic J2 of *G. tabacum* during early syncytia (Syn) development. (F) Same section as E showing specific binding of GR-ENG-1 antiserum to the SvG, but not within the developing syncytium. (G) Section through a tobacco root containing a sedentary parasitic J2 feeding from a well-developed syncytium. (H) Same section as G showing slight binding of GR-ENG-1 antiserum to the surface of the nematode, but not within the syncytium. Scale bars=50 μm. Sty=nematode stylet.

Various preferred embodiments of the present invention are set forth below. These embodiments are not intended to provide a detailed catalog of all manner in which the instant invention may be carried out, as numerous variations will be apparent to persons skilled in the arts to which the invention pertains. Accordingly, the following is set forth for illustrative purposes, and is not intended to be limiting of the invention.

1. Cyst and Root-Knot Nematodes

The invention may be carried out to protect plants from cyst (*Globodera* and *Heterodera* spp.) or root knot nematodes (*Meloidogyne* spp.). Cyst nematodes, like all plant-parasitic nematodes, are a microscopic roundworms very simple animal, related to the animal-parasitic roundworms that infect livestock and pets. The infective juvenile is the second-stage juvenile, so-called because it molts once in the egg from first-stage to second-stage. The infective juvenile is invisible to the naked eye. Its length is about ⅟64 inch. The juveniles penetrate roots and cause the formation of specialized feeding cells in the root's vascular system (veins). If the juvenile becomes a male, it leaves the root and moves through the soil and probably does not contribute further to plant damage. If the juvenile becomes a female, it loses the ability to move and swells to a lemon-shape as it matures. The young adult female is referred to as a white female. Plant damage is primarily due to the feeding of females. White females become yellow as they age and then brown after they die. The brown stage is the cyst for which the nematode is named. Each cyst can contain up to 500 eggs, but under field conditions usually contain many fewer eggs. The cyst protects the eggs from the soil environment.

Root-knot nematodes are sedentary endoparasites with an extremely intimate and complex relationship to the host plant. The infective second stage juvenile (J2) is free in the soil. Upon location of a host root, the J2 penetrates the root intercellularly in the region just posterior to the root cap and migrates to the developing vascular cylinder. The nematode then orients itself parallel to the cylinder and injects glandular secretions into the plant cells surrounding its head, resulting in the initiation of nematode feeding cells. These 5–7 cells undergo rapid nuclear divisions, increase tremendously in size, and become filled with pores and cell wall invaginations. The feeding site cells, or "giant cells", function as super transfer cells to provide nourishment to the developing nematode. During this time, the nematode loses the ability to move and swells from the normal eel shaped J2 to a large, pear shaped adult female. As the nematode feeds on the giant cells, parthenogenic reproduction results in the disposition of 300–400 eggs. This entire process occurs over the span of 20–30 days, and root-knot nematodes may complete as many as 7 generations during a cropping season. Thus, in addition to delivering at the feeding site a product that is toxic to the nematode, it will be seen that, by causing the plant itself to kill or disable the cells upon which the pathogen must feed, the pathogen will be much less successful at infecting the plant.

Feeding cells induced by cyst and root-knot nematodes (RKN), termed syncytia and giant-cells, respectively, are formed from host root cells during parasitism to sustain the growth and reproduction of the nematode (Hussey and Grundler (1998) Nematode parasitism of plants. In The physiology and biochemistry of free-living and plant-parasitic nematodes, ed. R. N. Perry, D. T. Wright, pp. 213–243, Wallingford UK: CABI publishing). Motile second-stage juveniles (J2) of the nematode penetrate plant roots and migrate to the vascular cylinder where the feeding cells serve as the sole nutritive source for the subsequent sedentary parasitic life stages of these nematodes. Evidence suggests that stylet (hollow feeding spear) secretions originating from three large unicellular esophageal gland cells of RKN and cyst nematodes play essential roles during parasitism of plant roots, including the induction of feeding cells (Davis, et al. (2000) *Annu. Rev. Phytopathol.* 38:341–372; Hussey (1989) *Annu. Rev. Phytopathol.* 27:123–141). Nematode secretions may directly or indirectly alter the development of affected host plant cells (Hussey (1989) *Annu. Rev. Phytopathol.* 27:123–141). This modification of normal plant cell development causes plant cells to re-differentiate into unique cell types strictly for the benefit of the nematode and is accompanied by multiple changes in plant gene expression (Bird, D. McK. (1996) *J. Parasitol.* 82:881–888).

Giant-cells and syncytia have several characteristics in common. In both cell types, there is an increase in metabolic activity and cytoplasmic density, the large central vacuole is reduced to several smaller ones, organelles proliferate, individual cells hypertrophy, cell walls thicken, and fingerlike protuberances (ingrowths) form along walls adjacent to the xylem vessels to increase membrane surface area for solute uptake (Hussey and Grundler (1998) Nematode parasitism of plants. In The physiology and biochemistry of free-living and plant-parasitic nematodes, ed. R. N. Perry, D. T. Wright, pp. 213–243, Wallingford UK: CABI publishing). The nuclei within these cells enlarge, develop an amoeboid appearance, have a very prominent nucleolus, and are polyploid. In giant-cells of RKN, the nuclei are stimulated to divide in the absence of cell division resulting in enlarged plant root cells containing hundreds of nuclei (Huang and Maggenti (1969) *Phytopathol.* 59:447–455). The syncytium of cyst nematodes is also multinucleate but arises via a different mechanism than that of giant-cells. Within the initial syncytial cell, the plasmodesmatal openings begin to gradually widen and wall degradation is initiated at pit fields (Jones (1981) *Ann. Appl. Biol.* 97:353–372; Grundler et al. (1998) *Eur. J. Plant Pathol.* 104:545–551). As the initial syncytial cell enlarges, the cell wall gaps expand and neighboring protoplasms fuse. Progressive cell wall dissolution allows the syncytium to expand longitudinally along the length of the vascular cylinder (extending as far as 2–3 mm) and can incorporate up to 200 plant cells (Jones (1981) *Ann. Appl. Biol.* 97:353–372).

2. Promoters

As used herein, a nematode responsive (or "nematode inducible") promoter refers to a promoter that (a) does not normally drive transcription in a plant cell except when that cell resides in tissue infected by a cyst or root knot nematode, or (b) normally drives transcription in a plant cell, and which drives increased levels of transcription when that cell resides in tissue infected by a cyst or root knot nematode. The promoter may be a naturally occurring promoter, may comprise a nematode responsive element isolated from a naturally occurring promoter, or may be a synthetic promoter.

A preferred promoter for use in the present invention is the endo-1,4-β-glucanase (Ntcel7) promoter of *Nicotiana tabacum* described herein. This promoter is referred to herein as a Nicotiana Ntcel7 promoter, and is set forth herein as SEQ ID NO: 9. The Nicotiana Ntcel7 promoter and other promoters that may be used to carry out the present invention are also disclosed in U.S. Pat. No. 6,005,092 to Shoseyov and Z. Shani, issued Dec. 21, 1999, the disclosure of which is incorporated by reference herein in its entirety.

Other DNAs that hybridize to a Nicotiana Ntcel7 promoter under high stringency hybridization conditions as described below, and which encode a nematode responsive promoter (particularly a cyst or root knot nematode responsive promoter) may also be used to carry out the present invention.

High stringency hybridization conditions which will permit homologous DNA sequences (e.g., other natural plant DNA sequences) to hybridize to a DNA sequence encoding a Nicotiana Ntcel7 promoter are well known in the art. For example, hybridization of such sequences to a DNA encoding a Nicotiana Ntcel7 promoter may be carried out in 25% formamide, 5×SSC, 5×Denhardt's solution, with 100 µg/ml of single stranded DNA and 5% dextran sulfate at 42° C., with wash conditions of 25% formamide, 5×SSC, 0.1% SDS at 42° C. for 15 minutes, to allow hybridization of sequences of about 60% homology. More stringent conditions are represented by a wash stringency of 0.3M NaCl, 0.03M sodium citrate, 0.1% SDS at 60° or even 70° C. using a standard in situ hybridization assay. (See Sambrook et al., Molecular Cloning, A Laboratory Manual (2d Ed. 1989) (Cold Spring Harbor Laboratory)). In general, plant DNA sequences which code for nematode responsive promoters and which hybridize to the DNA sequence encoding the nematode responsive elements disclosed herein will be at least 75%, 80%, 85%, 90% or even 95% homologous or more with the sequences of the DNA encoding the nematode responsive elements disclosed herein.

It will be apparent that other sequence fragments from the promoter 5' flanking region, longer or shorter sequences, or sequences with minor additions, deletions, or substitutions made thereto, can be prepared which will also encode a nematode responsive promoter, all of which are included within the present invention.

3. Heterologous DNAs and Expression Cassettes

DNA constructs, or "expression cassettes," of the present invention include, 5'-3' in the direction of transcription, a nematode responsive promoter of the present invention, a heterologous DNA segment operatively associated with the promoter, and, optionally, transcriptional and translational termination regions such as a termination signal and a polyadenylation region. All of these regulatory regions should be capable of operating in the transformed cells. The 3' termination region may be derived from the same gene as the transcriptional initiation region or from a different gene.

The term "operatively associated," as used herein, refers to DNA sequences contained within a single DNA molecule which are associated so that the function of one is affected by the other. Thus, a promoter is operatively associated with a gene when it is capable of affecting the expression of that gene (i.e., the gene is under the transcriptional control of the promoter). The promoter is said to be "upstream" from the gene, which is in turn said to be "downstream" from the promoter.

Heterologous DNAs used to carry out the present invention may encode any product that is disruptive of nematode attack when that DNA is transcribed (and, where applicable, translated) in a plant cell, including but not limited to proteins, peptides, and non-protein products such as antisense RNAs, ribozymes, other nucleic acids that suppress expression by sense strand suppression or triplex formation, etc. (see, e.g., U.S. Pat. No. 4,801,540 (Calgene, Inc.)).

The heterologous DNA may encode a product that is toxic to the plant cells, as described in U.S. Pat. No. 5,750,386 to Conkling et al. A wide variety of protein or peptide products which are toxic to plant cells can be used, including (but not limited to) enzymes capable of degrading nucleic acids (DNA, RNA) such as nucleases, restriction endonucleases micrococcal nucleas, Rnase A, and barnase; enzymes which attack proteins such as trypsin, pronase A, carboxypeptidase, endoproteinase Asp-N, endoproteinase Glu-C, and endoproteinase Lys-C; ribonucleases such as RNase CL-3 and RNase $T_1$, toxins from plant pathogenic bacteria such as phaseolotoxin, tabtoxin, and syringotoxin; lipases such as produced from porcine pancrease and Candida cyclindracea, membrane channel proteins such as glp F and connexins (gap junction proteins, and antibodies which bind proteins in the cell so that the cell is thereby killed or debilitated. Genes which produce antibodies to plant cell proteins can be produced as described in W. Huse et al. ((1989) *Science* 246:1275–1281). Proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase.

One preferred heterologous DNA is a structural gene encoding mature *Bacillus amyloliquefaciens* RNase (or Barnase). See, e.g., C. Mariani et al. ((1990) *Nature* 347:737–741) and C. Paddon and R. Hartley ((1985) *Gene* 40:231–39).

Note that the toxic product may either kill the plant cell in which it is expressed or simply disable the cell so that it is less capable of supporting the pathogen. It is preferred, particularly where the plant is a food plant, that the plant-toxic product be non-toxic to animals, and particularly be non-toxic to humans.

The heterologous DNA may encode any other product disruptive of nematode attack, including but not limited to those described in U.S. Pat. No. 5,589,622 to Gurr et al. (e.g., products toxic to the nematode). Thus the heterologous DNA may encode a *Bacillus thuringiensis* crystal protein toxic to insects. Strains of *B. thuringiensis* which produce polypeptide toxins active against nematodes are disclosed in U.S. Pat. Nos. 4,948,734 and 5,093,120 (Edwards et al.).

Again note that the toxic product may either kill the nematode attempting to feed on the plant cell in which it is expressed or simply disable the nematode so that it is less capable of feeding on the plant cell or establishing a feeding site. For example, the heterologous DNA may encode a peptide, antibody or the like that disrupts feeding by interacting with the ingestion or digestion of food such as one of the antibodies described for soybean cyst nematode including that against the dorsal pharyngeal gland (Atkinson et al, (1988) *Annals of Applied Biology* 112:459–469), modified as necessary for specificity to the root knot nematode, using the procedures for transgenic expression of antibodies in plants described by Hiatt, A. Gafferkey, R. C. & Bowdish, K. ((1989) Production of Antibodies in Transgenic Plants, *Nature* 342:76–78).

Again it is preferred, particularly where the plant is a food plant, that the nematode-toxic product be non-toxic to other animals, and particularly be non-toxic to birds, reptiles, amphibians, mammals and humans.

Where the expression product of the gene is to be located in a cellular compartment other than the cytoplasm, the structural gene may be constructed to include regions which code for particular amino acid sequences which result in translocation of the product to a particular site, such as the cell plasma membrane, or secretion into the periplasmic space or into the external environment of the cell. Various secretory leaders, membrane integration sequences, and translocation sequences for directing the peptide expression product to a particular site are described in the literature. See, for example, Cashmore et al., *Biotechnology* (1985) 3:803–808, Wickner and Lodish, *Science* (1985) 230:400–407.

The expression cassette may be provided in a DNA construct which also has at least one replication system. For convenience, it is common to have a replication system functional in *Escherichia coli*, such as ColE1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there may be at least one marker present, which may be useful in one or more hosts, or different markers for individual hosts. That is, one marker may be employed for selection in a prokaryotic host while another marker may be employed for selection in an eukaryotic host, particularly the plant host. The markers may provide protection against a biocide, such as antibiotics, toxins, heavy metals, or the like; may provide complementation by imparting prototrophy to an auxotrophic host; or may provide a visible phenotype through the production of a novel compound in the plant. Exemplary genes which may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are beta-glucuronidase (GUS) (providing indigo production), luciferase (providing visible light production), NPTII (providing kanamycin resistance or G418 resistance), HPT (providing hygromycin resistance), and the mutated aroA gene (providing glyphosate resistance).

An advantage of the present invention is that two or more promoters can be "daisychained" to a single structural gene. Where each promoter is responsive to a different pathogen, the plant is then provided with resistance to a plurality of promoters. For example, a second promoter may be positioned upstream from the structural gene and operatively associated therewith so that the structural gene is associated with a plurality of promoters, with each of the promoters activated by a different plant pathogen. Still more promoters can be included if desired. Other promoters that may be used in conjunction with the instant promoter are described in U.S. Pat. No. 5,750,386 to Conkling et al.

The various fragments comprising the various constructs, expression cassettes, markers, and the like may be introduced consecutively by restriction enzyme cleavage of an appropriate replication system and insertion of the particular construct or fragment into the available site. After ligation and cloning, the DNA construct may be isolated for further manipulation. All of these techniques are amply exemplified in the literature. See, e.g., Maniatis et al., Molecular Cloning: A Laboratory Manual, Cold Spring Harbor Laboratory, Cold Spring Harbor, N.Y. (1982).

4. Plant Transformation Vectors and Techniques

A vector is a replicable DNA construct. Vectors which may be used to transform plant tissue with DNA constructs of the present invention include both *Agrobacterium* vectors and ballistic vectors, as well as vectors suitable for DNA-mediated transformation. *Agrobacterium tumefaciens* cells containing a DNA construct of the present invention, wherein the DNA construct comprises a Ti plasmid, are useful in methods of making transformed plants. Plant cells are infected with an *Agrobacterium tumefaciens* to produce a transformed plant cell, and then a plant is regenerated from the transformed plant cell.

Numerous *Agrobacterium* vector systems useful in carrying out the present invention are known. For example, U.S. Pat. No. 4,459,355 discloses a method for transforming susceptible plants, including dicots, with an *Agrobacterium* strain containing the Ti plasmid. The transformation of woody plants with an *Agrobacterium* vector is disclosed in U.S. Pat. No. 4,795,855. Further, U.S. Pat. No. 4,940,838 to Schilperoort et al. discloses a binary *Agrobacterium* vector (i.e., one in which the *Agrobacterium* contains one plasmid having the vir region of a Ti plasmid but no T-DNA region, and a second plasmid having a T-DNA region but no vir region) useful in carrying out the present invention.

Microparticles carrying a DNA construct of the present invention, which microparticle is suitable for the ballistic transformation of a plant cell, are also useful for making transformed plants of the present invention. The microparticle is propelled into a plant cell to produce a transformed plant cell and a plant is regenerated from the transformed plant cell. Any suitable ballistic cell transformation methodology and apparatus can be used in practicing the present invention. Exemplary apparatus and procedures are disclosed in Sanford and Wolf, U.S. Pat. No. 4,945,050, and in Agracetus European Patent Application Publication No. 0 270 356, titled "Pollen-mediated Plant Transformation". When using ballistic transformation procedures, the expression cassette may be incorporated into a plasmid capable of replicating in the cell to be transformed. Examples of microparticles suitable for use in such systems include 1 to 5 $\mu$m gold spheres. The DNA construct may be deposited on the microparticle by any suitable technique, such as by precipitation.

Plant species may be transformed with the DNA construct of the present invention by the DNA-mediated transformation of plant cell protoplasts and subsequent regeneration of the plant from the transformed protoplasts in accordance with procedures well known in the art.

5. Plants for Transformation and Propagation of Transformants

Plants that may be used to carry out the present invention are typically vascular plants (including angiosperms and gymnosperms, monocots and dicots).

Cells used to carry out the present invention may be vascular plant cells, which may reside in vitro or in vivo in a plant tissue or intact plant, but other cell types such as bacterial cell may be employed to carry out intervening steps involved in preparing the DNA constructs employed in carrying out the present invention.

A transformed plant or host cell is a plant or host cell which has been transformed or transfected with DNA constructs as disclosed herein, using recombinant DNA techniques such as those described above coupled with propagation techniques such as those described below.

The promoter sequences disclosed herein may be used to express a heterologous DNA sequence in any plant species capable of utilizing the promoter (i.e., any plant species the RNA polymerase of which binds to the promoter sequences disclosed herein). Examples of plant species suitable for transformation with the DNA constructs of the present invention include both monocots and dicots, and include but are not limited to tobacco, soybean, potato, cotton, sugarbeet, sunflower, carrot, celery, flax, cabbage and other cruciferous plants, pepper, tomato, citrus trees, bean, strawberry, lettuce, maize, alfalfa, oat, wheat, rice, barley, sorghum and canola. Thus an illustrative category of plants which may be transformed with the DNA constructs of the present invention are the dicots, and a more particular category of plants which may be transformed using the DNA constructs of the present invention are members of the family Solanacae.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

6. Uses of the Invention

The present invention may be used in the manner described in U.S. Pat. No. 5,750,386 to Conkling et al. or U.S. Pat. No. 5,589,622 to Gurr et al. Thus, the present invention provides a method of controlling nematodes, comprising: (a) providing a cyst and root knot nematode-responsive promoter as described above, (b) preparing a construct as described above by combining said promoter with a further region which codes for a product disruptive of nematode attack, and (c) transforming plants with the construct to obtain plants which are cyst and root knot nematode resistant. The plants employed may be as described above, and transformation may be carried out as described above. Once a first generation ($F_O$ generation) of transformed plants are obtained, plant seed that contains the aforesaid construct, and that germinates into a cyst and root knot nematode resistant transgenic plant, may be produced from the $F_O$ plants by conventional breeding procedures. An agricultural field infected with cyst or root knot nematodes, or susceptible to cyst or root knot nematode infection, can then be planted with a crop of such plants in accordance with standard techniques (e.g., by planting seed or plantlets) to provide an agricultural field of crop plants that are resistant to cyst and/or root knot nematode infection.

The present invention is explained in greater detail in the following non-limiting Examples.

EXAMPLE 1

Plant and Nematode Culture Maintenance

Plant Material. Tobacco (*Nicotiana tabacum* 'NC95') seeds were surface sterilized with 2.5% sodium hypochlorite for five minutes, followed by several rinses with sterile water, and germinated in Petri plates containing 0.8% Noble agar (Fisher Scientific, Pittsburgh, Pa.) supplemented with Murashige and Skoog ((1962) *Physiol. Plant Path.* 15:473–497) minimal media, pH 5.8 and 3% sucrose. Tobacco seedlings were grown in a controlled temperature growth chamber at 25° C. with a 14-hour photoperiod.

Nematode Cultures and Inoculations. The tobacco cyst nematode (TCN), *Globodera tabacum* subspecies solanacearum (Miller and Gray (1972) *Nematologica* 18:404–413), and the root-knot nematode (RKN), *Meloidogyne incognita* Race 4 (Hartman and Sasser (1985) Identification of Meloidogyne species on the basis of differential host test and perineal—pattern morphology. In Advanced Treatise on Meloidogyne, Vol.II (Biology and Control), ed. J. N. Sasser and C. C. Carter, pp. 69–77, Raleigh, N.C.: NCSU Graphics) were propagated on greenhouse-grown tobacco (*Nicotiana tabacum* 'NC95') and tomato (*Lycopersicon esculentum* cv. Rutgers), respectively. To isolate cyst nematode eggs, TCN cysts were crushed gently in a glass homogenizer and the eggs were rinsed onto a 25 μm sieve. Hatching of TCN eggs was stimulated over filter-sterilized tobacco root diffusate (LaMondia (1995) *J. Nematol.* 27: 382–386) at 28° C. on a Baermann pan. RKN eggs were isolated from egg masses on tobacco roots with 0.5% sodium hypochlorite then rinsed with water and collected on a 25 μm sieve (Hussey and Barker (1973) *Plant Dis. Rep.* 57:1025–1028). RKN eggs were set up to hatch over water at 28° C. on a Baermann pan. After 3 days, hatched second-stage juveniles (J2) of either TCN or RKN were collected on a 25 μm sieve and surface-sterilized with 0.002% mercuric chloride, 0.002% sodium azide, and 0.001% Triton X-100 for 5 minutes followed by several washes with sterile water. Surface-sterilized J2 were resuspended in 50 μl of 2 mM Penicillin-G and 950 μl of 1.5% low melting agarose at 37° C. at a concentration of approximately 50 J2/10 μl for TCN and 5 J2/10 μl for RKN. Ten microliter aliquots of J2 were used to inoculate two week-old tobacco root tips.

EXAMPLE 2

In Planta Localization of TCN EGases Tissue

Fixation and Embedding. For immunolocalizations, TCN-infected root pieces were excised from Petri plates twenty-four to ninety-six hours after inoculation and fixed in 1% paraformaldehyde in phosphate-buffered saline (PBS; 137 mM NaCl, 1.4 mM $KH_2PO_4$, 2.6 mM KCl, 1.8 mM $Na_2HPO_4$, pH 7.4) for three hours at room temperature. After two 15 minute washes with PBS, the fixed root pieces were dehydrated in a graded ethanol series (30%, 60%, 70%, 85%, 95%, 100%, 15 min. each) and then incubated sequentially in ethanol: Histoclear (National Diagnostics, Atlanta, Ga.) 75:25, 50:50, 25:75 for 10 minutes each. After two 15 minutes incubations in 100% Histoclear, the root pieces were transferred to molten Paraplast plus (Fisher Scientific, Pittsburgh, Pa.) at 60° C. for two hours and embedded in blocks. For in situ mRNA localizations, nematode-infected tobacco root pieces were dissected from Petri plates 7–9 days or 12–14 days after infection and infiltrated with 4% paraformaldehyde (PFA) in phosphate-buffered saline (PBS; 130 mM NaCl, 7 mM $Na_2H_2PO_4$, 3 mM $NaH_2PO_4$) using a short vacuum. The root pieces were then transferred to fresh 4% PFA, incubated an additional 6 hours at room temperature followed by seventeen hours in 4% PFA at 4° C. The root pieces were washed twice in PBS for 20 minutes each time, dehydrated in a graded ethanol series (30%, 60%, 70%, 85%, 95%, 100%), incubated sequentially in Histo-clear (National Diagnostics, Atlanta, Ga.): ethanol 25:75, 50:50, 75:25, and then in 100% Histoclear twice for 30 minutes each time. The root pieces were incubated in Histoclear: Paraplast (Fisher Scientific) 75:25 overnight at 60° C., and then overnight again in pure Paraplast at 60° C. The Paraplast-embedded root pieces were sectioned to a thickness of 12μm (TCN-infected tobacco root tissue) or 20 μm (RKN-infected tobacco root tissue) using a rotary microtome (American Optical, Buffalo, N.Y.) and adhered to Superfrost Plus microscope slides (Fisher Scientific) overnight at 40° C. on a slide warmer. Three 15-minute incubations in Histoclear were used to remove the Paraplast from the sections followed by an ethanol series up to water to rehydrate the sections.

TCN-infected roots were sectioned to a thickness of 10 μm using a rotary microtome (American Optical, Buffalo, N.Y.) and placed on Superfrost Plus (Fisher Scientific) microscope slides. The sections were adhered to the slides overnight on a 40° C. slide warmer. Three 10-minute incubations in Histoclear at room temperature were used to remove the paraffin from the sections followed by rehydration in a graded ethanol series up to water. Non-specific binding sites in sections were blocked with 10% normal goat serum containing protease inhibitors (10 μl/ml of Stock A=0.1 mM leupeptin, 100 mM $Na_2EDTA$, 20 mM iodoacetamide, and Stock B=20 mM phenylmethylsulfonyl fluoride, 0.1 mM pepstatin A [all chemicals from Sigma, St. Louis, Mo.]) for three hours at room temperature. Primary antibody (GR-ENG1 mouse polyclonal sera; Smant, et al. (1998) *Proc. Natl. Acad. Sci. USA* 95:4906–491 1) diluted 1:100 with 10% goat serum in PBS was applied to the sections and incubated overnight at 4° C. After three five-minute rinses in PBS, secondary Alexa 488-goat anti-mouse IgG conjugate (Molecular Probes, Eugene, Oreg.) diluted 1:500 was applied to the sections and allowed to incubate in the dark for three hours at room temperature. The sections were rinsed three times for five minutes each in PBS before mounting with antiquenching agent (0.2 M carbonate buffer, pH 8.6, 50% glycerol, 0.02 mg/ml p-phenylenediamine). Sections were observed and photographed on an epifluorescence microscope (Zeiss, Oberkochen, Germany).

Endo-β-1,4-Glucanases In Planta. Antiserum raised against recombinant GR-ENG-1 (endoglucanase) of the potato cyst nematode (PCN), *Globodera rostochiensis* (Smant, et al. (1998) *Proc. Natl. Acad. Sci. USA* 95:4906–4911), was confirmed to bind to both GT-ENG-1 and GT-ENG-2 of the tobacco cyst nematode (TCN), *G. tabacum* (Goellner, et al. (2000) *J. Nematol.* 32:154–165). GR-ENG-1 antiserum did not bind to total protein preparations from either uninfected or TCN-infected tobacco roots on protein gel blots (data not shown). No staining was observed in plant tissue sections probed with mouse pre-immune sera, nor did the pre-immune sera bind to the nematode cuticle (FIG. 1A). Sections of infected roots at 24 hours after inoculation with J2 of TCN that were probed with GR-ENG-1 antiserum localized TCN EGases within the nematode and in tobacco root cortical tissue (FIG. 1B). Within the nematode, EGases were localized throughout the subventral esophageal gland cells including their extensions and terminating in the subventral gland ampullae at the base of the metacorpus (FIGS. 1C–1D). Within plant tissue, GR-ENG-1 antiserum localized TCN outside the head of the nematode and along the migratory path of the nematode through tobacco root tissue (FIGS. 1C–1D). Occasionally, the antiserum bound to the surface of the nematode, which may indicate the binding of EGases to the cuticle as the nematode migrated forward through root tissue (FIG. 1H).

To monitor the TCN EGases during the initiation of syncytia within host roots, tobacco roots inoculated with infective J2 were fixed for sectioning at 48–96 hours post-infection. The time of root penetration by J2 was monitored using an inverted microscope, and the stage of nematode development and extent of syncytium formation was determined in sections. EGases were not detected by GR-ENG-1 antiserum within initial syncytial cells during the early stages of formation, even when EGases were still detectable within the subventral gland cells of parasitic J2 (FIGS. 1E–1F). TCN EGases were also not detected within well-developed syncytia (FIGS. 1G–1H).

EXAMPLE 3

Isolation and Sequence Characterization of Tobacco EGases

To isolate poly A(+) RNA, 5 cm of infected or noninfected tobacco root pieces (excluding root tips) were excised from Petri plates and ground in a small glass homogenizer in 250 µl lysis-binding buffer (100 mM Tris-HCl, pH 7.5, 500 mM LiCl, 10 mM EDTA, pH 8.0, 5 mM dithiothreitol, 1% LiDS; Dynal, Lake Success, N.Y.). After lysis, the homogenate was centrifuged for one minute at 13,000×g and the supernatant was transferred to a clean tube. Twenty-five microliters of Dynal magnetic oligo-(dT)$_{25}$ beads equilibrated with lysis-binding buffer were added to the supernatant and placed on a rotator for 5 minutes to allow the mRNA to anneal to the beads. Using a magnetic stand the beads were washed twice in washing buffer with LiDS (10 mM Tris-HCl, pH 7.5, 0.15 M LiCl, 1 mM EDTA, 0.1% LiDS) and three times in washing buffer without LiDS. For first strand cDNA synthesis, the beads were washed several times in 1× first strand buffer (25 mM Tris-HCl, pH 8.3, 37.5 mM KCl, 1.5 mM MgCl$_2$) and then resuspended in 12 µl of RNase-free water. The following components were added to the bead suspension: 4 µl 5× first strand buffer, 2 µl 0.1 M DTT, 1 µl 10 mM dNTP mix, 1 µl Superscript II reverse transcriptase (200U/µl; GibCo BRL, Rockville, Md.). The reaction mixture was incubated on a rotator at 42° C. for one hour. Following first strand cDNA synthesis, two units of RNase H were added to the reaction and allowed to incubate at 37° C. for 20 minutes. The beads were rinsed twice with TE (10 mM Tris-HCl, pH8.0, 1 mM EDTA) and then resuspended in 25 µl of TE and stored at −20° C. Two degenerate primers to conserved amino acid domains of known plant EGase sequences were designed as follows: CWERPED: 5'-TGTTGGGARAGRCCHGARGAY-3' (SEQ ID NO:10) and YINAPL2: 5'-MACHADHGSWGCATTRAYRTAWGT-3' (SEQ ID NO:11) where R=A+G, Y=C+T, M=A+C, S=G+C, W=A+T, H=A+T+C, D=G+A+T. A ten microliter aliquot of first strand cDNA on the beads was washed with 1×PCR buffer (20 mM Tris-HCl, pH 8.4, 50 mM KCl) before adding the following reaction components: 5 µl 10×PCR buffer (200 mM Tris-HCl, pH8.4, 500 mM KC), 1.5 µl 50 mM MgCl$_2$, 1.0 µl 10 mM dNTP mix, 2.5 µl 10 µM 5' CWERPED, 2.5 µl 10 µM 3' YINAPL2, 27 µl dH$_2$0, and 2.5U Taq Polymerase). The PCR cycles were as follows: 1 cycle at 94° C. 2 min; 5 cycles at 94° C. 1 min., 37° C. 1 min., 72° C. 2 min with a ramp of 14° C./min between the annealing and elongation step (Compton, 1990); 35 cycles at 94° C. 30 sec, 50° C. 50 sec, 72° C. 1 cycle at 72° C. 10 min. A 1 kb amplified fragment was obtained and cloned into the pCR2.1 TA cloning vector (Invitrogen, Carlsbad, Calif.). Plasmid DNA was isolated from several individual transformants and the cDNA inserts were sequenced. Sequencing was carried out by The Interdisciplinary Center for Biotechnology Research (ICBR) DNA Sequencing Core Laboratory (DSEQ) located at the University of Florida, Gainsville, Fla. Isolation of the full-length tobacco EGase cDNAs was accomplished using 3' and 5' random amplification of cDNA ends systems (RACE, GibCo BRL) according to the manufacturer's protocols. The five tobacco EGase cDNA sequences were submitted to Genbank and have been designated with the following names and accession numbers; Ntcel2=AF362948 (SEQ ID NO:1), Ntcel4=AF362950, Ntcel5=AF362951, Ntcel7=AF362947 (SEQ ID NO:3), Ntcel8=AF362949 (SEQ ID NO:5).

Figure 3:
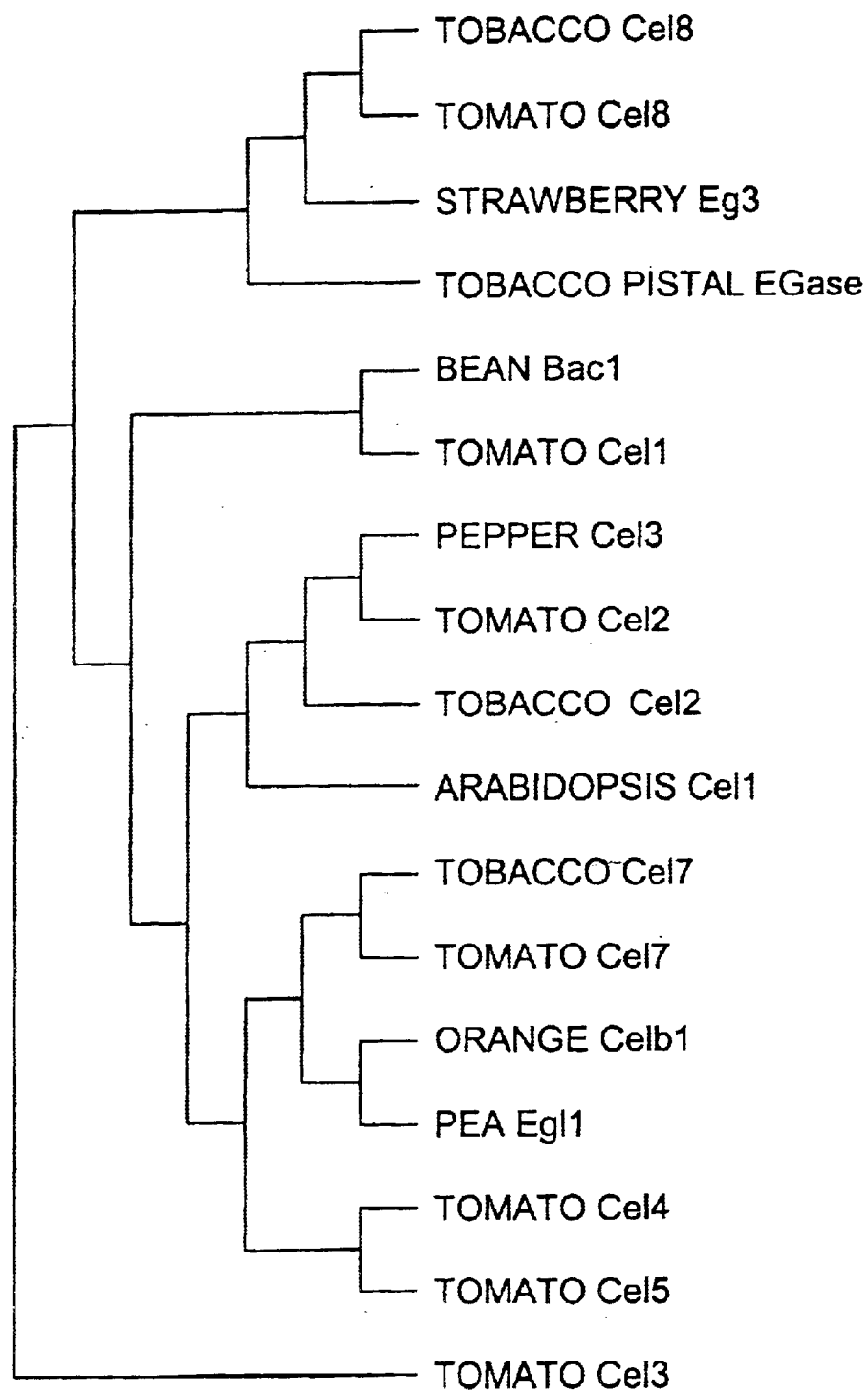
FIG. 3 illustrates a phylogenetic comparison of plant EGases. The evolutionary relationships among mature plant EGase amino acid sequences were calculated using programs of the Wisconsin Package Version 10.0, Seqweb Version 1.1 (Genetics Computer Group, Madison, Wis.) and the Kimura distance correction method (Kimura, 1983). The tree was constructed using the UPGMA method. Sequences used for the analysis (Genbank accession numbers in parentheses) were: *Arabidopsis* Cel1 (X98544); Bean Bac1 (M57400); Orange Celb1 (AF000136); Pea Egl1 (L41046); Pepper Cel3 (X97189); Tobacco Pistal EGase (AF128404); Tobacco Cel1 (AF362949), Cel2 (AF362948), Cel4 (AF362950), Cel5 (AF362951), Cel7 (AF362947); Tomato Cel1 (U13054), Cel2 (U13055), Cel3 (U78526), TPP18/Cel4 (U20590), Cel5 (AF077339), Cel7 (Y1 1268), Cel8 (AF098292); Strawberry Eg3 (AJ006349).
Figure 5:
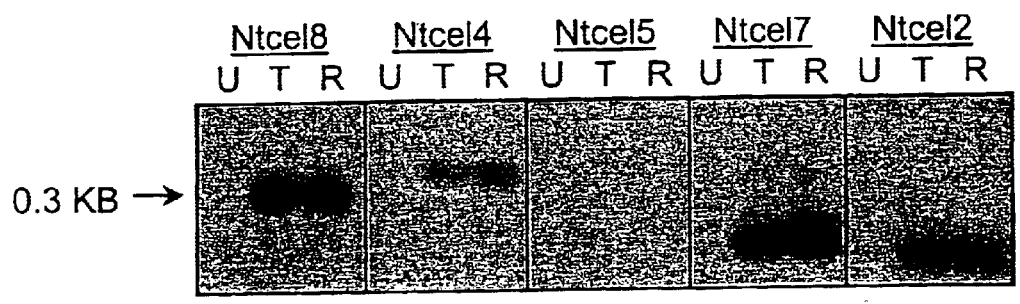
FIG. 5 shows the relative RT-PCR analysis of tobacco EGase transcripts in uninfected and nematode-infected root tissue. RT-PCR products were amplified from uninfected (U), tobacco cyst nematode-infected (T), or root knot nematode-infected (R) tobacco root tissue 7–9 days post-infection using tobacco EGase gene-specific primers. A DNA gel blot of the RT-PCR products was probed with tobacco EGase digoxigenin-labeled DNA probes. L=1 kb DNA ladder (GibCo BRL, Rockville, Md.).

FIG. 2 shows the 1 kb cDNA product amplified by RT-PCR from TCN-infected tobacco root tissue (data not shown) using primers designed to two conserved amino acid domains (CWERPEDM (SEQ ID NO:7) and YINAPL (SEQ ID NO:8)) present in plant EGases. No observable products were amplified from identical uninfected root tissue. Five distinct tobacco EGase cDNA sequences representing structurally divergent gene family members were identified after sequencing random clones of the 1 kb product and designated as Ntcel2, Ntcel4, NtCel5, Ntcel7, and Ntcel8 based on the nomenclature described by del Campillo ((1999) Multiple endo-1,4-β-D-glucanase (Cellulase) genes in *Arabidopsis*. In Current Topics in Developmental Biology, Volume 46, ed. R. A. Pedersen and G. P. Schatten, pp. 39–61. New York: Academic Press). Full-length coding sequences of three of these cDNA clones (Ntcel2, Ntcel7, and Ntcel8) were obtained using 3' and 5' RACE PCR (FIG. 2). The 1 kb partial cDNA sequences of Ntcel4 and Ntcel5 showed the highest percentage nucleotide and amino acid sequence identity with tomato Cel4 and Cel5, respectively (Brummell, et al. (1997) *Plant Mol. Biol.* 33:87–95; del Campillo and Bennett (1996) *Plant Physiol.* 111:813–820), and were not characterized further due to their low expression levels (see below). A phylogenetic tree constructed using mature amino acid sequences of Ntcel2 (SEQ ID NO:2), Ntcel7 (SEQ ID NO:4), and Ntcel8 (SEQ ID NO:6), and 14 other plant EGase sequences depicts the relatedness of the new tobacco EGases with selected members of the plant EGase gene family (FIG. 3). The 1500 bp open reading frame (ORF) of the 1674 bp Ntcel2 cDNA clone encodes a 500-amino acid polypeptide, including a 35-mer putative signal peptide (FIG. 2). The mature protein has a deduced molecular mass of 51.3 kDa and a pI of 8.7. Ntcel2 has 54% nucleotide and amino acid sequence identity to Ntcel7 and 55% nucleotide and 49% amino acid identity to Ntcel8. Ntcel2 shares significant amino acid similarity with pepper Cel3 (89%; Trainotti, et al. (1998) *Hereditas* 128:121–126), tomato Cel2 (86%; Lashbrook, et al. (1994) *Plant Cell* 6:1485–1493), and Arabidopsis Cell (73%; Shani, et al. (1997) *Plant Mol. Biol.* 34:837–842) (FIG. 3). The 1467 bp ORF of the 1723 bp Ntcel7 cDNA clone encodes a 489-amino acid polypeptide, including a putative signal peptide corresponding to amino acids 1–24 (FIG. 2). The mature protein has a deduced molecular mass of 51.8 kDa and pI of 8.7. Analysis of the predicted amino acid sequence of Ntcel7 showed 52% nucleotide and 49% amino acid identity with Ntcel8. Ntcel7 shares significant amino acid sequence similarity with tomato Cel7 (86%; Catala, et al. (1997) *Plant Journal* 12:417–426), orange Celb1 (71%; Burns, J. K. et al., 1997, unpub.; Accession #AF000136 ), and pea Egl1 (68%; Wu, et al. (1996) *Plant Physiol.* 111:163–170) (FIG. 5). The 1872 bp ORF of the 2286 bp Ntcel8 cDNA clone encodes a 624-amino acid polypeptide, including a 28-mer putative signal peptide (FIG. 2). The mature protein has a deduced molecular mass of 65.7 kDa and a pI of 8.0. This tobacco EGase shares significant amino acid similarity to tomato Cel8 (81%; Catala and Bennett (1998) *Plant Physiol.* 118:1535) and strawberry Eg3 (79%; Trainotti, et al. (1999) *Plant Mol. Biol.* 40:323–332). Amino acid sequence alignment of all three tobacco EGases depicts the extra 124 amino acids at the C-terminus of Ntcel8 that are absent from Ntcel2 and Ntcel7 (FIG. 2).

DNA Gel Blot Analysis. Tobacco genomic DNA was isolated from young leaves using the DNeasy Plant Maxi isolation kit (Qiagen, Valencia, Calif.). Genomic DNA (5 µg) was digested separately with EcoRI, BamHI, and HindIII, electrophoresed on a 0.7% (w/v) agarose gel, and transferred to Hybond-N membrane (Amersham, Arlington Heights, Ill.). Tobacco genomic DNA was hybridized with DIG-labeled tobacco EGase DNA probes corresponding to the 1 kilobase (kb) nucleotide sequence spanning the two conserved amino acid domains, CWERPED (SEQ ID NO:7) and YINAPL (SEQ ID NO:8), described above. Hybridizations were carried out in standard hybridization buffer (5×SSC, 0.1% N-lauroylsarcosine, 0.02% SDS, 1% blocking reagent [Roche Molecular, Indianapolis, Ind.]) at 65° C. for 18 hours followed by three 10-minute washes in 2×SSC at room temperature. The membrane was then washed twice at 68° C. with 0.5×SSC for 30 minutes, and twice at 68° C. with 0.1×SSC for 30 minutes. After incubating the membranes in 1% blocking reagent for 1 hour, the membranes were incubated with a 1:10,000 dilution of sheep anti-DIG alkaline phosphatase conjugate for 30 minutes. Unbound antibody was removed by three 15 minutes washes with maleic acid wash buffer (0.1 M maleic acid, 0.15 M NaCl, pH 7.5, 0.3% Tween-20). The membrane was incubated in AP detection buffer (100 mM Tris-HCl, pH 9.5, 100 mM NaCl, 50 mM $MgCl_2$) for 10 minutes followed by a 1:100 dilution of the chemiluminescent substrate CSPD (Roche Molecular) prior to wrapping the membrane in saran wrap and exposing it to x-ray film for 2.5 hours.

Figure 4:
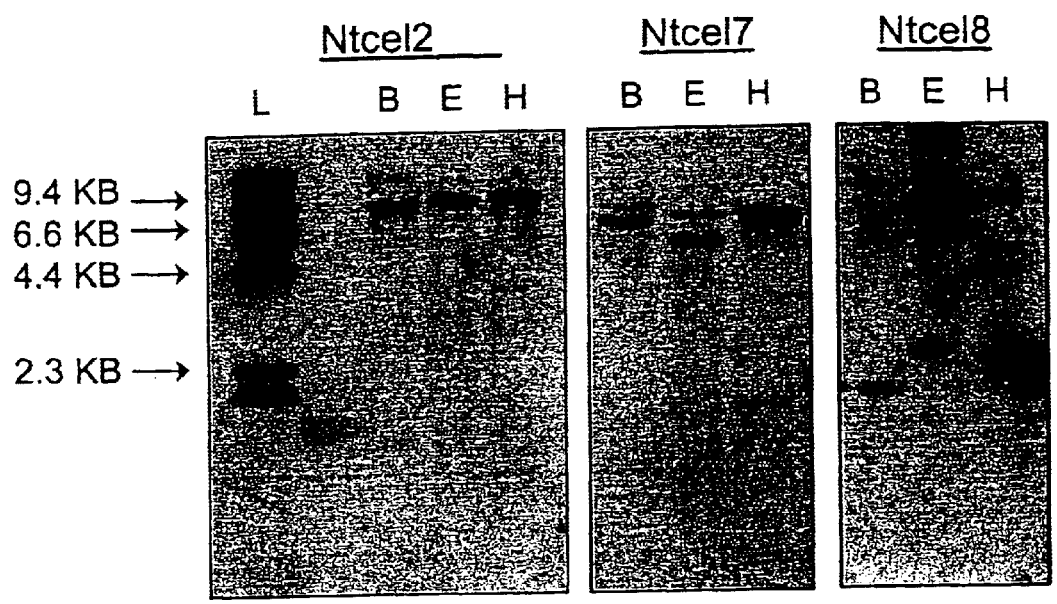
FIG. 4 shows DNA gel blot analysis of Ntcel2, Ntcel7, and Ntcel8 genes in tobacco. Genomic DNA (5 μg) was digested with BamHI, EcoRI, and HindIII, electrophoresed on a 0.7% agarose gel, blotted to nylon membranes, and probed with a 1 kb fragment spanning the conserved amino acid domains, CWERPED (SEQ ID NO:7) and YINAPL (SEQ ID NO:8), of Ntcel2, Ntcel7, and Ntcel8. Blots were hybridized in 5×SSC at 65° C. and washed twice in 0.5×SSC at 68° C. and twice in 0.1×SSC at 68° C. B=BamHI, E=EcoRI, and H=HindIII.

FIG. 4 shows DNA gel blots of BamHI, EcoRI, and HindIII-digested tobacco genomic DNA which were hybridized separately with 1 kb probes generated to sequences spanning two conserved amino acid domains of Ntcel2, Ntcel7, and Ntcel8 (CWERPEDM (SEQ ID NO:7) and YINAPL (SEQ ID NO:8); FIG. 2). High stringency genomic analysis suggests that a single gene may encode Ntcel2. In contrast, both Ntcel7 and Ntcel8 appear to belong to small gene families (FIG. 4).

EXAMPLE 4

Upregulation of Tobacco EGases in Nematode-Infected Roots

RT-PCRs were conducted both on mRNA extracted from equivalent amounts of total RNA or mRNA isolated from equivalent amounts of nematode-infected tobacco root tissue. The same results were obtained using either method. Total RNA was isolated using the Puregene RNA isolation kit (Gentra Systems, Minneapolis, Minn.) according to the manufacturer's instructions and treated with RNase-free DNase I (2 U/μl; Ambion, Austin, Tex.). The DNase I was removed using DNA-free (Ambion) acccording to the manufacturer's protocol. Oligo-dT magnetic beads (Dynal) were used to extract mRNA from 500 ng of total RNA or directly from tissue ground in lysis-binding buffer as described in EXAMPLE 3. The mRNA was eluted from the beads at 65° C. for 2 min in 11.5 μl of DEPC-treated water. First strand cDNA's were synthesized using a 3' degenerate tobacco EGase primer including a BamHI restriction site (3 ' Tobcelribo BamHI: 5'-CGCGGATCCGGRTTRTYWCCHAR HAWRTARTCHACYTG-3' (SEQ ID NO:12) where R=A+ G, Y=C+T, W=A+T, H=A+T+C) that recognized all five tobacco EGase cDNA sequences. Reverse transcription reactions contained the following components: 4 μl 5×first strand buffer (250 mM Tris, pH 8.3, 375 mM KCl, 15 mM $MgCl_2$), 2 μl 0.1M DTT, 1 μl 10 mM dNTP mix, 0.5 μl 10 μM 3' Tobcelribo BamHI primer, 11.5 μl mRNA isolated from above, and 1 μl Superscript reverse transcriptase (200 U/μl; GibCo BRL). The reaction was incubated at 42° C. for 1 hour, followed by the addition of 2 Units of RNase H (GibCo BRL) and an additional 20-minute incubation at 37° C. The cDNA was precipitated and resuspended in 10 μl of water. Reactions without the addition of reverse transcriptase were included as a control for contaminating DNA, although amplifications of tobacco genomic DNA using each EGase primer set did not generate fragments of the size predicted for amplification from cDNA. 5' gene-specific primers containing an EcoRI restriction site and the 3' Tobcelribo BamHI primer were used in subsequent PCR amplification reactions. 5' primer sequences were as follows: 5 'Tobcel2 EcoRI: 5'-CCGGAATTCGTAACATGCAGCATGTGACATCC-3' (SEQ ID NO:13); 5' Tobcel4 EcoRI: 5'-CCGGAA TTCGCATGTTGGAGCAAGGATCTTC-3' (SEQ ID NO:14); 5' Tobcel5 EcoRI: 5'-CCGGAATTCCCAGGC TCACCTAG CTTTCAAGC-3' (SEQ ID NO:15); 5' Tobcel7EcoRI: 5'-CCGGAATTCGGG GGCCTAATTTAC AAGCTAAC-3' (SEQ ID NO:16); 5' Tobcel8 EcoRI: 5'-CCGGAATTCCCATGCACCTGTGTTTGAGAAG TAC-3' (SEQ ID NO:17). PCR reactions contained the following components: 5 μl 10×PCR buffer (200 mM Tris, pH 8.4, 500 mM KCl), 1.5 μl 50 mM $MgCl_2$, 1.0 μl 10 mM dNTP mix, 2.5 μl 5' primer, 2.5 μl 3' primer, 2 μl cDNA, 35 μl water, 0.5 μl Taq polymerase (5 U/μl ). PCR cycles consisted of an initial denaturation step at 94° C. for 2 minutes, followed by 40 cycles of 94° C. 1 min, 55° C. 1 min, 72° C. 2 min, and a final 10 min elongation step at 72° C. Ten microliter aliquots of each RT-PCR reaction were electrophoresed on a 2% agarose gel, transferred to nylon membranes, and hybridized with corresponding tobacco EGase DIG-labeled DNA probes.

To compare the relative expression of individual tobacco EGase genes in noninfected and nematode-infected (RKN or TCN) tobacco root tissue, the presence of EGase mRNA was analyzed by reverse transcription-polymerase chain reaction (RT-PCR). Gene-specific primer sets designed to each of the five tobacco EGase cDNA sequences amplified the following sized fragments: Ntcel2–181 bp; Ntcel4–350 bp; Ntcel5–245 bp; Ntcel7–209 bp; Ntcel8–300 bp (FIG. 5). These same size fragments were not amplified from tobacco genomic DNA or from control reactions that did not contain reverse transcriptase, excluding the possibility of contaminating genomic DNA in the results. Equivalent amounts of either RNA or root tissue were used for the synthesis of first-strand cDNAs, and the relative amount of amplification products were consistently higher in nematode-infected roots as compared to uninfected roots for each tobacco EGase gene, in three separate experiments (FIG. 5). When the entire uninfected root PCR reaction was loaded on a gel only a faint band could be detected (data not shown). DNA gel blots of amplified fragments hybridized with probes to each tobacco EGase cDNA confirmed the identity of the products (FIG. 5). The three genes showing the highest expression levels (Ntcel2, Ntcel7, Ntcel8) were selected for further analysis.

EXAMPLE 5

In Situ Localization of Tobacco EGase Transcripts in Root-Knot Nematode-Infected Roots Digoxigenin-Labeled RNA Probes. Antisense and sense RNA probes were synthesized to Ntcel2, Ntcel7, and Ntcel8 EGase cDNAs by in vitro transcription. Gene-specific primer sets containing EcoRI and BamHI restriction sites were designed to each of the three tobacco EGase cDNA sequences and used to amplify products ranging in size from 150–210 basepairs (bp). The 5' Tobcel2 EcoRI primer and 5' Tobcel 7 EcoRI primers were used together with the 3' Tobcelribo BamHI primer (see EXAMPLE 4) to amplify products of 181 bp and 209 bp, respectively of Ntcel2 and Ntcel7. 5' Tobcel8–2 EcoRI: 5'-CCGGAATTCCGTCTT TCGGAACAGCAACCCT-3' (SEQ ID NO:18), and 3' Tobcel8–2 BamHI: 5'-CGCGGATCCTTCATCTGCGT ATCCACTGACAG-3' (SEQ ID NO:19) were used to amplify a 150 bp fragment from Ntcel8. Two primers designed to conserved regions of plant 18S ribosomal RNA genes were used to amplify a 87 bp fragment of the tobacco 18S ribosomal RNA gene to be used as a control riboprobe. Primers sequences were as follows: Plant 18S 5' EcoRI: 5'-CCGGAATTCGAATGATCCGGTGAAGTGTTCGG-3' (SEQ ID NO:20) and Plant 18S 3 ' BamHI: 5'-CGCGGA TCCGATAAGGTTTAGTGGACTTCTCGC-3' (SEQ ID NO:21). Each product was digested with both EcoRI and BamHI and cloned into a pBluescript SK+ transcription vector with a truncated multiple cloning site (De Boer, et al. (1998) J. Nematol. 30: 309–312) and flanking T3 and T7 promoter sequences. Purified plasmid DNA corresponding to each tobacco riboprobe clone was digested separately with EcoRI and BamHI, column purified, and 1–2 µg was added to in vitro transcription reactions containing digoxigenin-UTP (Roche Molecular) and the respective polymerase to synthesize RNA probes. Unincorporated nucleotides were removed using mini Quick Spin RNA columns (Roche Molecular) and the incorporation of DIG-UTP was quantified by dot blot analysis.

In Situ RNA Hybridization. Rehydrated tissue sections were pre-treated with proteinase K (1 µg/ml (12 µm sections) or 2 µg/ml (20 µm sections) in 100 mM Tris-HCl and 50 mM EDTA, pH 8.0) for 30 minutes at 37° C., rinsed for 5 minutes twice with TBS buffer (150 mM NaCl and 10 mM Tris-HCl, pH 7.5), incubated in TBS with glycine (2 mg/ml) for 2 minutes, and then washed again for 5 minutes twice with TBS buffer. Sections were post-fixed with 4% paraformaldehyde in PBS for 5 minutes and washed in TBS for 5 minutes. After acetylation with acetic anhydride (0.25% in 0.1 M triethanolamine-HCl, pH 8.0) for 10 minutes, the sections were washed with TBS, dehydrated in a graded ethanol series, and air-dried. Hybridization solution (40% formamide, 10% dextran sulfate, 1 mg/ml yeast tRNA, 0.5 mg/mL polyadenylic acid, 0.3 M NaCl, 0.01 M Tris-HCl, pH 6.8, 0.01 M sodium phosphate, pH 6.8, 5 mM EDTA, 40 U/mL ribonuclease inhibitor) was supplemented with 100 ng of DIG-labeled riboprobe per 100 µl of hybridization solution and dispensed onto slides containing sections. Hybridization was carried out for 16–18 hours at 45° C. in a humid chamber. Post-hybridization treatments included a 20-minute wash with 2×SSC at room temperature followed by RNase A treatment (50 µg/mL in 0.5 M NaCl, 10 mM Tris-HCl, pH 7.5, and 1 mM EDTA) for 30 minutes at 37° C. Slides were then washed in 0.2×SSC twice for one hour at 55° C., and once with 0.1×SSC for thirty minutes at 55° C. Slides were rinsed in TBST (0.1 M Tris-HCl, pH 8.0, 0.15 M NaCl, and 0.3% Triton X-100) for 10 minutes on a shaking platform and then blocked overnight at 4° C. with 2% bovine serum albumin (BSA) fraction V (Fisher) in TBST. Hybridized DIG-labeled transcripts were immunolocalized by incubating sections with a 1:200 dilution of sheep anti-digoxigenin-alkaline phosphatase conjugate (Roche Molecular) in 1% BSA in TBST for two hours at room temperature. The slides were washed three times for 15 minutes each with TBST and once with alkaline phosphatase (AP) detection buffer (0.1 M Tris-HCl, pH 9.5, 0.1 M NaCl, and 50 mM $MgCl_2$) for 10 minutes. Substrate buffer (175 µg/mL 5-bromo-4-chloro-3-indolyl phosphate and 350 µg/mL nitroblue tetrazolium chloride in AP detection buffer) was dispensed onto sections on slides and color development was allowed to proceed for 4–8 hours at room temperature in the dark. Slides were washed with water before mounting with 50% glycerol, 7% gelatin, and 1% phenol. Sections were photographed using a Zeiss Axiophot microscope (Zeiss, Oberkochen, Germany) equipped with Nomarski differential interference contrast optics.

Figure 6:
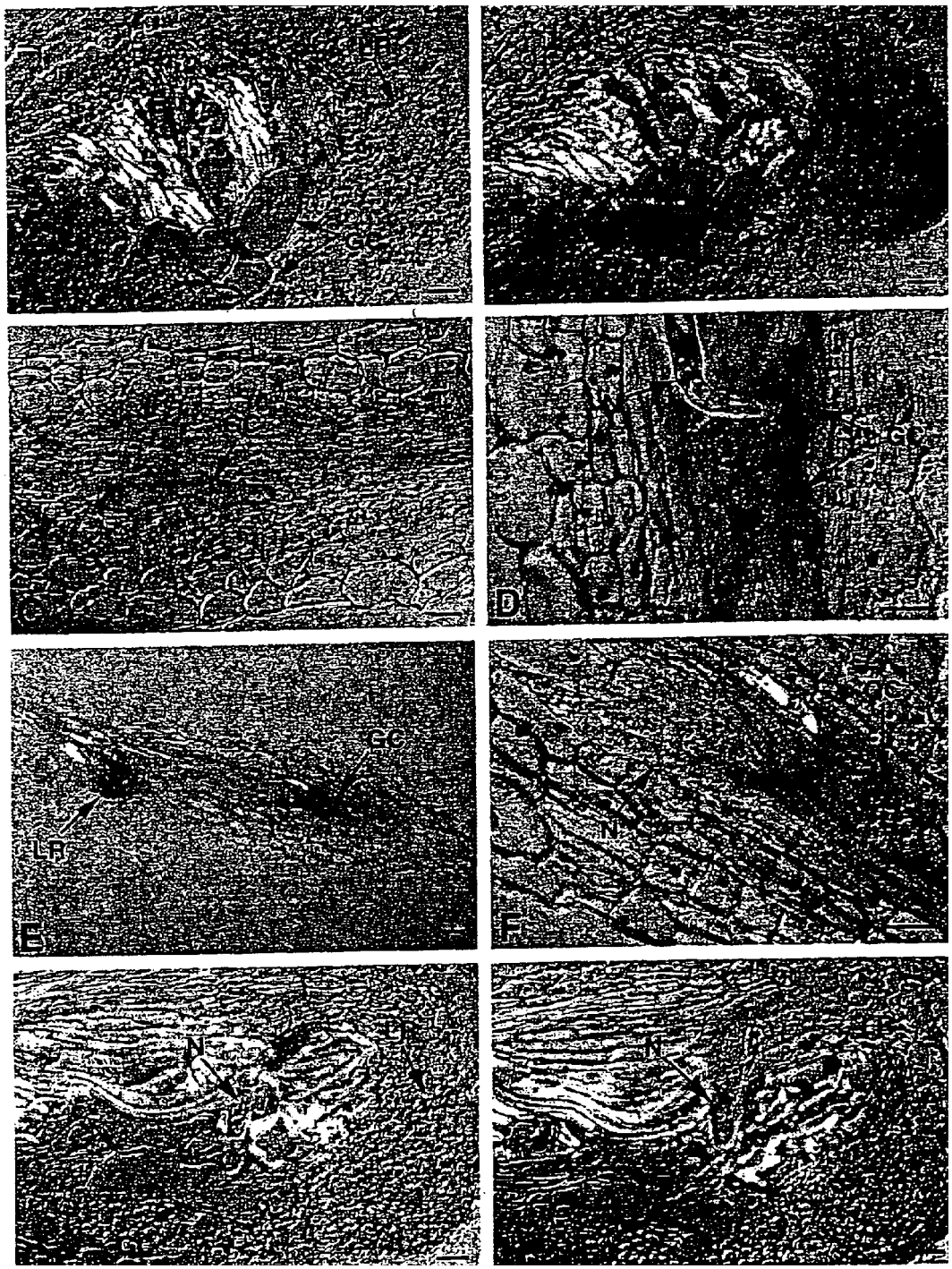
FIG. 6 shows in situ hybridization of Ntcel7, Ntcel8, and Ntcel2 mRNA in root knot kematode (RKN)-infected tobacco roots. Longitudinal serial sections through a RKN-induced gall on tobacco roots 12–14 days post-infection (dpi) and hybridized with a tobacco Ntcel7 sense (A) or antisense digoxigenin (DIG)-labeled riboprobe (B). Longitudinal section through a RKN-induced gall on tobacco roots 7–9 dpi and hybridized with a tobacco Ntcel7 antisense DIG-labeled riboprobe (C). Longitudinal sections through tobacco roots infected with RKN and hybridized with a tobacco Ntcel8 antisense DIG-labeled riboprobe at 7–9 dpi (D-F). Longitudinal serial sections through a tobacco gall induced by RKN at 12–14 dpi and hybridized with a tobacco Ntcel2 sense (G) and antisense (H) DIG-labeled riboprobe. N=nematode, GC=giant cells, LR-lateral root. Scale bars=50 μm.

Results. To determine the spatial expression pattern of tobacco Ntcel2, Ntcel7, and Ntcel8 EGases in nematode-infected root tissue, mRNA in situ hybridizations were conducted on sections cut at weekly timepoints from developing tobacco galls after inoculation with RKN. RT-PCR experiments indicated that tobacco EGase expression levels were relatively low; therefore serial sections were cut to a thickness of 20 µm to increase transcript volume for detecting hybridization signals. FIG. 6 depicts longitudinal sections through RKN-infected root galls hybridized with either antisense or sense tobacco EGase riboprobes. FIGS. 6A and 6B illustrate giant cell-specific expression of Ntcel7 in serial sections through an RKN-induced tobacco gall 12–14 days after infection. Strong labeling was detected within the giant-cells and lateral root primordia (FIG. 6B) in sections probed with the antisense Ntcel7 riboprobe, but not in sections probed with a sense Ntcel7 riboprobe (FIG. 6A). FIG. 6C also depicts strong expression of Ntcel7 in developing giant-cells during early stages of nematode development (7–9 days post-infection), but not in surrounding cortical parenchyma cells. Sections probed with tobacco 18S ribosomal RNA sense and antisense riboprobes were used as controls. Strong hybridization signal was detected in all gall tissues with the antisense, but not the sense 18S RNA probe (data not shown).

In situ mRNA hybridizations using tobacco Ntcel8 sense and antisense riboprobes showed a similar expression pattern to that of Ntcel7 in sections of RKN-induced gall tissues (FIG. 6). During early stages of infection (7–9 dpi), Ntcel8 transcripts were localized specifically within developing giant-cells and lateral root primordia when probed with an antisense Ntcel8 riboprobe (FIGS. 6D-F), but not a sense riboprobe (data not shown). During later stages of infection (12–14 dpi), Ntcel8 transcripts were still detected in giant-cells (data not shown). Consistently, signal intensity for Ntcel7 was stronger than for Ntcel8, but it is unclear if this reflects a true quantitative difference in expression levels.

Tobacco Ntcel2 sense and antisense riboprobes were used to probe sections through RKN-induced gall tissue, (FIGS. 6G and 6H). In sections probed with the Ntcel2 antisense riboprobe the overall signal intensity was much lower than signal intensities observed in sections probed with either Ntcel7 or Ntcel8 antisense riboprobes. Weak hybridization of Ntcel2 was detected in giant-cells and in lateral root primordia at 12–14 days post-infection with an antisense Ntcel2 riboprobe (FIG. 6H), but not a sense Ntcel2 riboprobe (FIG. 6G).

EXAMPLE 6

Figure 7:
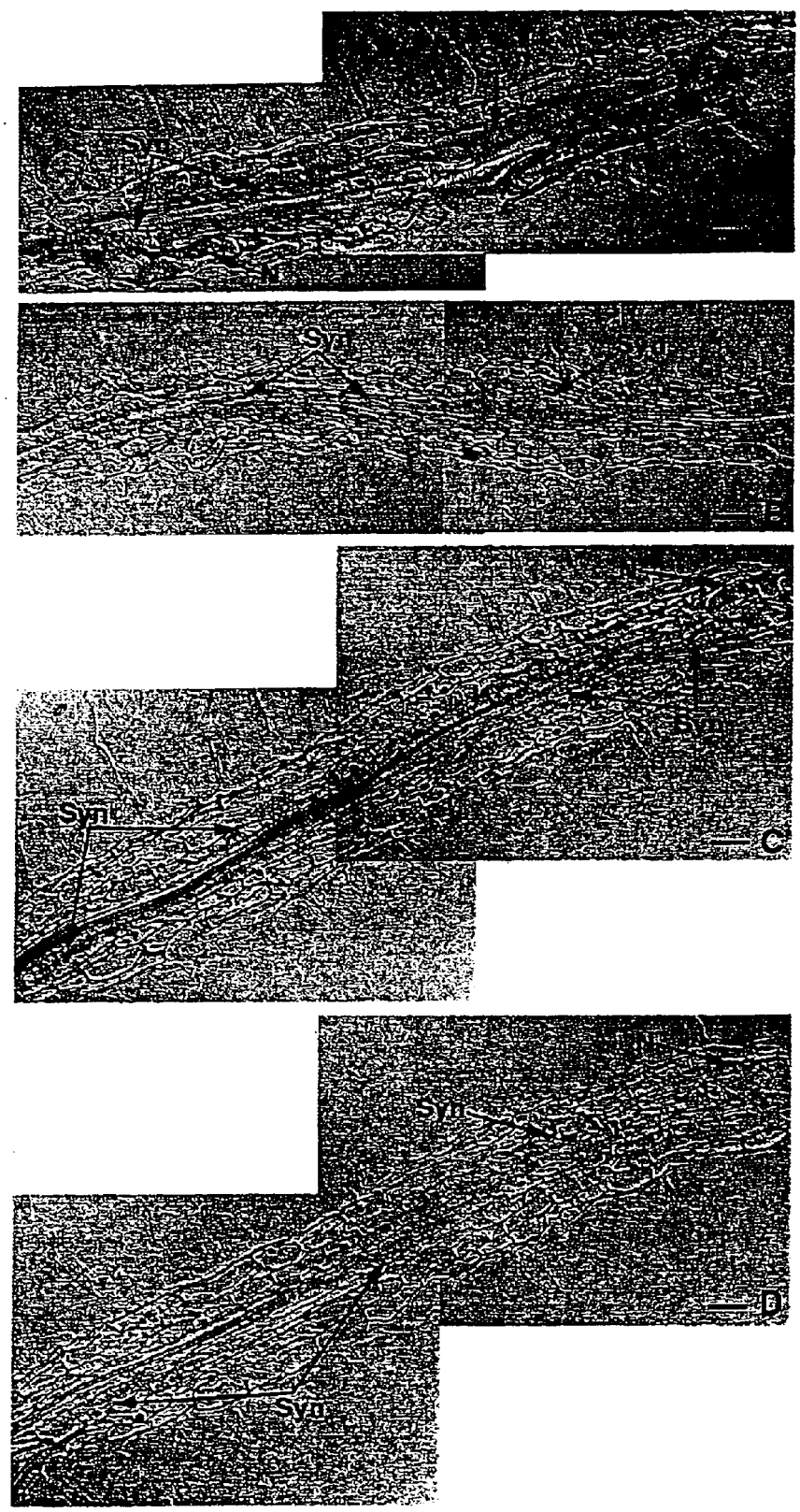
FIG. 7 shows in situ hybridization of tobacco Ntcel7 and Ntcel8 mRNA in tobacco cyst nematode-infected tobacco roots. Longitudinal serial sections through tobacco roots infected with tobacco cyst nematodes (TCN) and hybridized with a tobacco Ntcel7 antisense (A) or sense (B) digoxigenin (DIG)-labeled riboprobe 7 days post-infection. Longitudinal serial sections through tobacco roots infected with TCN and hybridized with a tobacco Ntcel8 antisense (C) or sense (D) DIG-labeled riboprobe 7 days post-infection. N=nematode, S=syncytia. Scale bars=50 μm.

In Situ Localization of Tobacco EGase Transcripts in Cyst Nematode-Infected Roots To determine the spatial expression pattern of tobacco Ntcel2, Ntcel7, and Ntcel8 EGases in TCN-infected root tissue, mRNA in situ hybridizations were conducted on sections cut from TCN-infected tobacco roots at 7 days post-infection (FIG. 7). Longitudinal serial sections through TCN-infected tobacco roots were cut to a thickness of 12 µm because roots were much thinner than RKN-induced galls and to increase the number of sections containing nematodes. Thinner sectioning may have contributed to a slight loss in hybridization signal intensity (target transcript) as compared to in situ hybridizations of RKN-infected root tissue (20 μm thick). In situ hybridizations of tobacco EGase riboprobes to TCN-infected root tissue sections required 6 hours of color development, in contrast to 2–4 hour color development for hybridizations of RKN-infected root tissue sections.

Longitudinal sections through TCN-infected tobacco roots were treated with antisense or sense tobacco Ntcel2, Ntcel7, Ntcel8, and 1 8S ribosomal RNA riboprobes. FIG. 7 shows strong expression of Ntcel7 in TCN-induced syncytia at 7 days after inoculation in sections probed with an antisense (FIG. 7A), but not a sense (FIG. 7B) Ntcel7 riboprobe. Ntcel7 transcripts were also detected in lateral root tips with the antisense, but not the sense Ntcel7 riboprobe as observed in RKN-infected tobacco root tissue (data not shown).

In situ mRNA hybridizations using tobacco Ntcel8 antisense and sense riboprobes showed a similar expression pattern to that of Ntcel7 in sections of TCN-infected root tissues (FIGS. 7C and 7D). At 7 days post-infection, Ntcel8 transcripts were localized within developing TCN-induced syncytia when probed with an antisense Ntcel8 riboprobe (FIG. 7C), but not a sense Ntcel8 riboprobe (FIG. 7D). Hybridization signal intensity was much stronger for Ntcel7 than for Ntcel8 and may reflect a quantitative difference in transcript levels, as was observed for these probes when hybridized to RKN-infected tobacco root tissue. Ntcel8 transcripts were also detected in lateral root tips with the anti sense, but not the sense Ntcel8 riboprobes. In situ mRNA hybridizations using tobacco Ntcel2 sense and antisense riboprobes did not show an observable difference in hybridization signal intensity (data not shown). Ntcel2 transcript levels may not be high enough for detection using this method. Sections probed with control tobacco 18S ribosomal RNA antisense and sense riboprobes produced strong hybridization signals in all cell types, but were more intense within TCN-induced syncytia (data not shown).

The foregoing is illustrative of the present invention, and is not to be construed as limiting thereof. The invention is defined by the following claims, with equivalents of the claims to be included therein.

That which is claimed is:

1. A nucleic acid construct which comprises:
   (a) the isolated promoter of SEQ ID NO:9 ; and
   (b) a heterologous nucleic acid operably linked to said isolated promoter, wherein said heterologous nucleic acid encodes a nematocidal or insecticidal protein or peptide.

2. The nucleic acid construct according to claim 1, wherein said heterologous nucleic acid encodes an insecticidal protein.

3. The nucleic acid construct according to claim 2, wherein said heterologous nucleic acid encodes a *Bacillus thuringiensis* crystal protein toxic to insects.

4. The nucleic acid construct according to claim 1, wherein said heterologous nucleic acid encodes a product toxic to plant cells.

5. The nucleic acid construct according to claim 1, wherein said nucleic acid construct is a plasmid.

6. A plant cell transformed with a nucleic acid construct according to claim 1.

7. A method of producing a transformed plant, comprising regenerating a plant from the plant cell according to claim 6.

8. An *Agrobacterium tumefaciens* cell containing the nucleic acid construct according to claim 5, wherein said nucleic acid construct is a Ti plasmid.

9. A method of producing a transformed plant, comprising infecting a plant cell with the *Agrobacterium tumefaciens* cell according to claim 8 to produce a transformed plant cell, and regenerating a plant from said transformed plant cell.

10. A microparticle comprising the nucleic acid construct according to claim 1, wherein said microparticle is for plant transformation.

11. A method of making a transformed plant, comprising propelling the microparticle according to claim 10 into a plant cell to produce a transformed plant cell, and regenerating a plant from said transformed plant cell.

12. A plant cell protoplast comprising a nucleic acid construct according to claim 1.

13. A method of making a transformed plant, comprising regenerating a plant from the plant cell protoplast according to claim 12.

14. A transformed plant comprising transformed plant cells, said transformed plant cells containing the nucleic acid construct according to claim 1.

15. The transformed plant according to claim 14, wherein said plant is a dicot.

16. The transformed plant according to claim 14, wherein said plant is a monocot.

17. The transformed plant according to claim 14, wherein said plant is a tobacco (*Nicotiana tabacum*) plant.

18. A transformed seed produced from the transformed plant according to claim 14.

19. A method of producing a cyst and root knot nematode resistant plant, comprising the steps of:

(a) providing a DNA construct comprising the isolated promoter of SEQ ID NO: 9 operably linked to a heterologous nucleic acid encoding a nematocidal protein or peptide, and (b) transforming a plant with the nucleic acid construct to produce a cyst and root knot nematode resistant plant.

20. The method according to claim 19, wherein said plant is a monocot.

21. The method according to claim 19, wherein said plant is a dicot.

22. A plant produced by the method of claim 19.

23. An isolated nucleic acid comprising the isolated promoter of SEQ ID NO: 9.

* * * * *

SEQUENCE LISTING

<160> NUMBER OF SEQ ID NOS: 21

<210> SEQ ID NO 1
<211> LENGTH: 1674
<212> TYPE: DNA
<213> ORGANISM: Nicotiana tabacum
<220> FEATURE:
<221> NAME/KEY: CDS
<222> LOCATION: (12)..(1514)
<223> OTHER INFORMATION:

<400> SEQUENCE: 1

```
agcaactaaa t atg gcg cga aaa aat tgc ggc ttt ccg gca ggt ttc ccg      50
            Met Ala Arg Lys Asn Cys Gly Phe Pro Ala Gly Phe Pro
            1               5                   10 tca ttt ccc ctt agt cta gct ctc att ttc ttc ctc ccc gtc aat ccc        98
Ser Phe Pro Leu Ser Leu Ala Leu Ile Phe Phe Leu Pro Val Asn Pro
    15                  20                  25 ctc cgg cat tgc tct gcc ggt ggc cat gac tac cgc gac gcc ctc cga       146
Leu Arg His Cys Ser Ala Gly Gly His Asp Tyr Arg Asp Ala Leu Arg
30                  35                  40                  45 aaa agc atc ctc ttc ttc gaa ggc caa cgc tcc ggc aaa ctt cca ccc       194
Lys Ser Ile Leu Phe Phe Glu Gly Gln Arg Ser Gly Lys Leu Pro Pro
                50                  55                  60 gac caa cgt ata aag tgg cgt aaa gac tcc gcc ttg tac gat ggc gcc       242
Asp Gln Arg Ile Lys Trp Arg Lys Asp Ser Ala Leu Tyr Asp Gly Ala
            65                  70                  75 tcc gcc gga gtg gac ttg aca gga ggt tac tat gat gcc ggg gac aac       290
Ser Ala Gly Val Asp Leu Thr Gly Gly Tyr Tyr Asp Ala Gly Asp Asn
        80                  85                  90 gtc aaa ttc gtc ttt cca atg gcg ttc act acc aca ttg ttg tcg tgg       338
Val Lys Phe Val Phe Pro Met Ala Phe Thr Thr Thr Leu Leu Ser Trp
    95                  100                 105 agc ata ata gac ttc aaa agg aac atc gga cgt gag ctt gga aac gcc       386
Ser Ile Ile Asp Phe Lys Arg Asn Ile Gly Arg Glu Leu Gly Asn Ala
110                 115                 120                 125 gtg aag gca gtg aag tgg gcg acg gat ttc ttg tta aaa gcg acg gct       434
Val Lys Ala Val Lys Trp Ala Thr Asp Phe Leu Leu Lys Ala Thr Ala
```

```
                    130              135              140
aag gaa ggc gtc ata tat gtg caa gtg ggt gat gca ttt tct gac cat        482
Lys Glu Gly Val Ile Tyr Val Gln Val Gly Asp Ala Phe Ser Asp His
                145              150              155 agc tgt tgg gag agg cca gaa gat atg gac act ttg aga act gtt tac        530
Ser Cys Trp Glu Arg Pro Glu Asp Met Asp Thr Leu Arg Thr Val Tyr
            160              165              170 aag att gac cag aat cat cct gga tca gac gtc gcc ggc gaa atc gct        578
Lys Ile Asp Gln Asn His Pro Gly Ser Asp Val Ala Gly Glu Ile Ala
        175              180              185 gcc tct ttg gcc gcc gcg tcc att gtt ttc cgg tca ctc gac tct tct        626
Ala Ser Leu Ala Ala Ala Ser Ile Val Phe Arg Ser Leu Asp Ser Ser
190              195              200              205 tac tct ggt ctc cta ctt gat cgt gcc gtt aaa gtt ttc gag ttt gcc        674
Tyr Ser Gly Leu Leu Leu Asp Arg Ala Val Lys Val Phe Glu Phe Ala
                210              215              220 aac agg cac aga ggt gca tac agc tcc agt ttg cac tct gcg gtt tgc        722
Asn Arg His Arg Gly Ala Tyr Ser Ser Ser Leu His Ser Ala Val Cys
            225              230              235 cct ttt tac tgt gat ttt gat gga tac cag gac gaa ttg ctt tgg ggt        770
Pro Phe Tyr Cys Asp Phe Asp Gly Tyr Gln Asp Glu Leu Leu Trp Gly
        240              245              250 gcg gcg tgg cta cac aaa gca acg agg agg cgt caa tac aga gag tac        818
Ala Ala Trp Leu His Lys Ala Thr Arg Arg Arg Gln Tyr Arg Glu Tyr
255              260              265 ata gtg aaa aac gag gtt gtt tta aga gct gga gac acc att aat gaa        866
Ile Val Lys Asn Glu Val Val Leu Arg Ala Gly Asp Thr Ile Asn Glu
270              275              280              285 ttc ggt tgg gat aat aaa cac gct ggg att aat gtc ctc att tcc aag        914
Phe Gly Trp Asp Asn Lys His Ala Gly Ile Asn Val Leu Ile Ser Lys
                290              295              300 gag gtg ttg atg gga aga gca cca gac cta aaa tcc ttt caa gta aat        962
Glu Val Leu Met Gly Arg Ala Pro Asp Leu Lys Ser Phe Gln Val Asn
            305              310              315 gca gat gcc ttc atc tgc tca ata tta cct gga att tct cat ccc caa       1010
Ala Asp Ala Phe Ile Cys Ser Ile Leu Pro Gly Ile Ser His Pro Gln
        320              325              330 gtg caa tat tct ccg ggt gga ctc att gtc aaa cct ggc gtt tgt aac       1058
Val Gln Tyr Ser Pro Gly Gly Leu Ile Val Lys Pro Gly Val Cys Asn
335              340              345 atg cag cat gtg aca tcc ttg tcc ttc cta ctg ctc gct tac tct aat       1106
Met Gln His Val Thr Ser Leu Ser Phe Leu Leu Leu Ala Tyr Ser Asn
350              355              360              365 tat cta agc cac gcc aat cat gcc gtg cca tgt ggc tcc atc tca gcc       1154
Tyr Leu Ser His Ala Asn His Ala Val Pro Cys Gly Ser Ile Ser Ala
                370              375              380 acc cct gct ctc ctc aaa cat att gcc aaa cgt cag gtg gat tac att       1202
Thr Pro Ala Leu Leu Lys His Ile Ala Lys Arg Gln Val Asp Tyr Ile
            385              390              395 ctt gga gat aat ccg caa aga atg tca tac atg gtg ggg tat ggt cca       1250
Leu Gly Asp Asn Pro Gln Arg Met Ser Tyr Met Val Gly Tyr Gly Pro
        400              405              410 cgt tac cca tta agg att cac cac aga ggt agc tct tta cca tct gtg       1298
Arg Tyr Pro Leu Arg Ile His His Arg Gly Ser Ser Leu Pro Ser Val
415              420              425 gcg gcc cac cca gcc cgt att ggg tgc aaa gga ggg tcc aat tat ttc       1346
Ala Ala His Pro Ala Arg Ile Gly Cys Lys Gly Gly Ser Asn Tyr Phe
430              435              440              445 tta tca cca aat cca aat cca aat cgc ttg att ggt gct gtt gtt ggt       1394
```

-continued

```
Leu Ser Pro Asn Pro Asn Pro Asn Arg Leu Ile Gly Ala Val Val Gly
            450                 455                 460 ggg ccc aat ata act gat tcc ttc cca gac gca agg cca ttc ttt cag      1442
Gly Pro Asn Ile Thr Asp Ser Phe Pro Asp Ala Arg Pro Phe Phe Gln
            465                 470                 475 gag tcg gag ccc act act tac gtt aat gcg cca ttg gtg ggc ctt ttg      1490
Glu Ser Glu Pro Thr Thr Tyr Val Asn Ala Pro Leu Val Gly Leu Leu
            480                 485                 490 gct tac ttt tca gcc cat act tga tctcttccaa tttaagaga aatagagtg       1544
Ala Tyr Phe Ser Ala His Thr
            495                 500 gtgtgcaaag gccaccctct ctataccata tattattatt gttcaacatt ctatttcttc    1604
cttattcaat caacgaagaa actactacgc ctaaaaaaaa aaaaaaaaaa aaaaaaaaa     1664 gaaaaaaaaa                                                            1674

<210> SEQ ID NO 2
<211> LENGTH: 500
<212> TYPE: PRT
<213> ORGANISM: Nicotiana tabacum

<400> SEQUENCE: 2

Met Ala Arg Lys Asn Cys Gly Phe Pro Ala Gly Phe Pro Ser Phe Pro
1               5                   10                  15

Leu Ser Leu Ala Leu Ile Phe Phe Leu Pro Val Asn Pro Leu Arg His
            20                  25                  30

Cys Ser Ala Gly Gly His Asp Tyr Arg Asp Ala Leu Arg Lys Ser Ile
        35                  40                  45

Leu Phe Phe Glu Gly Gln Arg Ser Gly Lys Leu Pro Pro Asp Gln Arg
    50                  55                  60

Ile Lys Trp Arg Lys Asp Ser Ala Leu Tyr Asp Gly Ala Ser Ala Gly
65                  70                  75                  80

Val Asp Leu Thr Gly Gly Tyr Tyr Asp Ala Gly Asp Asn Val Lys Phe
                85                  90                  95

Val Phe Pro Met Ala Phe Thr Thr Thr Leu Leu Ser Trp Ser Ile Ile
            100                 105                 110

Asp Phe Lys Arg Asn Ile Gly Arg Glu Leu Gly Asn Ala Val Lys Ala
        115                 120                 125

Val Lys Trp Ala Thr Asp Phe Leu Leu Lys Ala Thr Ala Lys Glu Gly
    130                 135                 140

Val Ile Tyr Val Gln Val Gly Asp Ala Phe Ser Asp His Ser Cys Trp
145                 150                 155                 160

Glu Arg Pro Glu Asp Met Asp Thr Leu Arg Thr Val Tyr Lys Ile Asp
                165                 170                 175

Gln Asn His Pro Gly Ser Asp Val Ala Gly Glu Ile Ala Ala Ser Leu
            180                 185                 190

Ala Ala Ala Ser Ile Val Phe Arg Ser Leu Asp Ser Ser Tyr Ser Gly
        195                 200                 205

Leu Leu Leu Asp Arg Ala Val Lys Val Phe Glu Phe Ala Asn Arg His
    210                 215                 220

Arg Gly Ala Tyr Ser Ser Ser Leu His Ser Ala Val Cys Pro Phe Tyr
225                 230                 235                 240

Cys Asp Phe Asp Gly Tyr Gln Asp Glu Leu Leu Trp Gly Ala Ala Trp
                245                 250                 255

Leu His Lys Ala Thr Arg Arg Arg Gln Tyr Arg Glu Tyr Ile Val Lys
            260                 265                 270
```

```
Asn Glu Val Val Leu Arg Ala Gly Asp Thr Ile Asn Glu Phe Gly Trp
        275                 280                 285

Asp Asn Lys His Ala Gly Ile Asn Val Leu Ile Ser Lys Glu Val Leu
        290                 295                 300

Met Gly Arg Ala Pro Asp Leu Lys Ser Phe Gln Val Asn Ala Asp Ala
305                 310                 315                 320

Phe Ile Cys Ser Ile Leu Pro Gly Ile Ser His Pro Gln Val Gln Tyr
                325                 330                 335

Ser Pro Gly Gly Leu Ile Val Lys Pro Gly Val Cys Asn Met Gln His
            340                 345                 350

Val Thr Ser Leu Ser Phe Leu Leu Ala Tyr Ser Asn Tyr Leu Ser
        355                 360                 365

His Ala Asn His Ala Val Pro Cys Gly Ser Ile Ser Ala Thr Pro Ala
        370                 375                 380

Leu Leu Lys His Ile Ala Lys Arg Gln Val Asp Tyr Ile Leu Gly Asp
385                 390                 395                 400

Asn Pro Gln Arg Met Ser Tyr Met Val Gly Tyr Gly Pro Arg Tyr Pro
                405                 410                 415

Leu Arg Ile His His Arg Gly Ser Ser Leu Pro Ser Val Ala Ala His
            420                 425                 430

Pro Ala Arg Ile Gly Cys Lys Gly Gly Ser Asn Tyr Phe Leu Ser Pro
        435                 440                 445

Asn Pro Asn Pro Asn Arg Leu Ile Gly Ala Val Val Gly Gly Pro Asn
450                 455                 460

Ile Thr Asp Ser Phe Pro Asp Ala Arg Pro Phe Gln Glu Ser Glu
465                 470                 475                 480

Pro Thr Thr Tyr Val Asn Ala Pro Leu Val Gly Leu Leu Ala Tyr Phe
                485                 490                 495

Ser Ala His Thr
            500

<210> SEQ ID NO 3
<211> LENGTH: 1723
<212> TYPE: DNA
<213> ORGANISM: Nicotiana tabacum
<220> FEATURE:
<221> NAME/KEY: CDS
<222> LOCATION: (45)..(1514)
<223> OTHER INFORMATION:

<400> SEQUENCE: 3
ctaaacaagc catttatac tttgagcaaa tcaaaaaaag tata atg gcg ttt aga        56
                                             Met Ala Phe Arg
                                               1 gtg gaa gtt tct gtt tgc atc att ctc ttc tca tca ttt ttc ttc tct       104
Val Glu Val Ser Val Cys Ile Ile Leu Phe Ser Ser Phe Phe Phe Ser
  5                  10                  15                  20 ttg ggt act gcc caa ggg gtt ttc aac tat aga gag gct ctt gaa aag       152
Leu Gly Thr Ala Gln Gly Val Phe Asn Tyr Arg Glu Ala Leu Glu Lys
                 25                  30                  35 tcc att ttg ttc ttt gaa gga caa aga tca ggg aaa ctc ccc cat aac       200
Ser Ile Leu Phe Phe Glu Gly Gln Arg Ser Gly Lys Leu Pro His Asn
             40                  45                  50 cag cgt gtc tct tgg agg ggt agt tcg ggg ctt tca gat ggt tca ctt       248
Gln Arg Val Ser Trp Arg Gly Ser Ser Gly Leu Ser Asp Gly Ser Leu
         55                  60                  65 gct aaa gtg gac tta act gga ggc tat tat gat gct gga gac aat gtc       296
```

|     |     |     |     |     |     |     |     |     |     |     |     |     |     |     |      |
|-----|-----|-----|-----|-----|-----|-----|-----|-----|-----|-----|-----|-----|-----|-----|------|
| Ala | Lys | Val | Asp | Leu | Thr | Gly | Gly | Tyr | Tyr | Asp | Ala | Gly | Asp | Asn | Val  |
|     | 70  |     |     |     | 75  |     |     |     | 80  |     |     |     |     |     |      |

| aag | ttc | aat | ttc | cca | atg | gca | tac | act | acc | aca | ttg | ctc | tct | tgg | aac | 344 |
|-----|-----|-----|-----|-----|-----|-----|-----|-----|-----|-----|-----|-----|-----|-----|-----|-----|
| Lys | Phe | Asn | Phe | Pro | Met | Ala | Tyr | Thr | Thr | Thr | Leu | Leu | Ser | Trp | Asn |     |
| 85  |     |     |     | 90  |     |     |     | 95  |     |     |     | 100 |     |     |     |     |

| aca | ctt | gag | tat | ggc | aag | aga | atg | ggg | ccc | caa | ttg | caa | aat | gca | cgg | 392 |
|-----|-----|-----|-----|-----|-----|-----|-----|-----|-----|-----|-----|-----|-----|-----|-----|-----|
| Thr | Leu | Glu | Tyr | Gly | Lys | Arg | Met | Gly | Pro | Gln | Leu | Gln | Asn | Ala | Arg |     |
|     |     |     |     | 105 |     |     |     |     | 110 |     |     |     |     | 115 |     |     |

| gca | gct | atc | cgt | tgg | gcc | acc | gat | tac | tta | ctc | aaa | tgc | gca | aat | gct | 440 |
|-----|-----|-----|-----|-----|-----|-----|-----|-----|-----|-----|-----|-----|-----|-----|-----|-----|
| Ala | Ala | Ile | Arg | Trp | Ala | Thr | Asp | Tyr | Leu | Leu | Lys | Cys | Ala | Asn | Ala |     |
|     |     |     | 120 |     |     |     |     | 125 |     |     |     |     | 130 |     |     |     |

| gcg | ccc | aac | aag | ctc | ttc | gtt | ggg | gtt | ggt | gac | cca | aat | tct | gat | cat | 488 |
|-----|-----|-----|-----|-----|-----|-----|-----|-----|-----|-----|-----|-----|-----|-----|-----|-----|
| Ala | Pro | Asn | Lys | Leu | Phe | Val | Gly | Val | Gly | Asp | Pro | Asn | Ser | Asp | His |     |
|     |     | 135 |     |     |     |     | 140 |     |     |     |     | 145 |     |     |     |     |

| aaa | tgt | tgg | gaa | agg | ccc | gaa | gat | atg | gat | act | gtc | cgg | agc | gtc | tat | 536 |
|-----|-----|-----|-----|-----|-----|-----|-----|-----|-----|-----|-----|-----|-----|-----|-----|-----|
| Lys | Cys | Trp | Glu | Arg | Pro | Glu | Asp | Met | Asp | Thr | Val | Arg | Ser | Val | Tyr |     |
|     |     | 150 |     |     |     |     | 155 |     |     |     |     | 160 |     |     |     |     |

| tat | gtc | tct | ccg | agc | agt | cct | ggc | tct | gat | gtg | gct | gga | gaa | atg | gcc | 584 |
|-----|-----|-----|-----|-----|-----|-----|-----|-----|-----|-----|-----|-----|-----|-----|-----|-----|
| Tyr | Val | Ser | Pro | Ser | Ser | Pro | Gly | Ser | Asp | Val | Ala | Gly | Glu | Met | Ala |     |
| 165 |     |     |     |     | 170 |     |     |     |     | 175 |     |     |     |     | 180 |     |

| gct | gct | tta | gct | gct | gcc | tca | tta | gtt | ttc | cgg | acg | gtt | gat | ccg | gtt | 632 |
|-----|-----|-----|-----|-----|-----|-----|-----|-----|-----|-----|-----|-----|-----|-----|-----|-----|
| Ala | Ala | Leu | Ala | Ala | Ala | Ser | Leu | Val | Phe | Arg | Thr | Val | Asp | Pro | Val |     |
|     |     |     |     | 185 |     |     |     |     | 190 |     |     |     |     | 195 |     |     |

| tac | tca | aag | aag | cta | ttg | gga | aat | gca | gtg | aaa | gta | ttt | aga | ttt | gca | 680 |
|-----|-----|-----|-----|-----|-----|-----|-----|-----|-----|-----|-----|-----|-----|-----|-----|-----|
| Tyr | Ser | Lys | Lys | Leu | Leu | Gly | Asn | Ala | Val | Lys | Val | Phe | Arg | Phe | Ala |     |
|     |     |     | 200 |     |     |     |     | 205 |     |     |     |     | 210 |     |     |     |

| gtt | caa | tac | aga | ggc | tcc | tat | agt | gat | tca | cta | ggc | tct | gca | gct | tgc | 728 |
|-----|-----|-----|-----|-----|-----|-----|-----|-----|-----|-----|-----|-----|-----|-----|-----|-----|
| Val | Gln | Tyr | Arg | Gly | Ser | Tyr | Ser | Asp | Ser | Leu | Gly | Ser | Ala | Ala | Cys |     |
|     |     |     | 215 |     |     |     |     | 220 |     |     |     |     | 225 |     |     |     |

| cca | ttc | tac | tgc | tca | tac | tct | ggt | tat | aag | gat | gag | cta | tat | tgg | gga | 776 |
|-----|-----|-----|-----|-----|-----|-----|-----|-----|-----|-----|-----|-----|-----|-----|-----|-----|
| Pro | Phe | Tyr | Cys | Ser | Tyr | Ser | Gly | Tyr | Lys | Asp | Glu | Leu | Tyr | Trp | Gly |     |
|     | 230 |     |     |     |     | 235 |     |     |     |     | 240 |     |     |     |     |     |

| gct | gca | tgg | cta | ttg | aga | gca | aca | aat | gat | att | tca | tac | tta | aac | ttc | 824 |
|-----|-----|-----|-----|-----|-----|-----|-----|-----|-----|-----|-----|-----|-----|-----|-----|-----|
| Ala | Ala | Trp | Leu | Leu | Arg | Ala | Thr | Asn | Asp | Ile | Ser | Tyr | Leu | Asn | Phe |     |
| 245 |     |     |     |     | 250 |     |     |     |     | 255 |     |     |     |     | 260 |     |

| ata | aac | aca | ttg | gga | gcc | aat | gat | gta | cca | gac | tta | ttt | agc | tgg | gat | 872 |
|-----|-----|-----|-----|-----|-----|-----|-----|-----|-----|-----|-----|-----|-----|-----|-----|-----|
| Ile | Asn | Thr | Leu | Gly | Ala | Asn | Asp | Val | Pro | Asp | Leu | Phe | Ser | Trp | Asp |     |
|     |     |     |     | 265 |     |     |     |     | 270 |     |     |     |     | 275 |     |     |

| aac | aag | tat | gct | ggt | gct | cat | gtt | ctt | atg | gca | agg | aga | agc | gtt | gtt | 920 |
|-----|-----|-----|-----|-----|-----|-----|-----|-----|-----|-----|-----|-----|-----|-----|-----|-----|
| Asn | Lys | Tyr | Ala | Gly | Ala | His | Val | Leu | Met | Ala | Arg | Arg | Ser | Val | Val |     |
|     |     |     | 280 |     |     |     |     | 285 |     |     |     |     | 290 |     |     |     |

| gga | aat | gac | aaa | agg | ttt | gat | cca | ttc | aga | caa | caa | gct | gaa | gac | ttt | 968 |
|-----|-----|-----|-----|-----|-----|-----|-----|-----|-----|-----|-----|-----|-----|-----|-----|-----|
| Gly | Asn | Asp | Lys | Arg | Phe | Asp | Pro | Phe | Arg | Gln | Gln | Ala | Glu | Asp | Phe |     |
|     |     |     | 295 |     |     |     |     | 300 |     |     |     |     | 305 |     |     |     |

| gtt | tgc | aaa | ata | cta | ccc | aac | tca | cct | tat | aca | agt | acc | caa | tat | aca | 1016 |
|-----|-----|-----|-----|-----|-----|-----|-----|-----|-----|-----|-----|-----|-----|-----|-----|------|
| Val | Cys | Lys | Ile | Leu | Pro | Asn | Ser | Pro | Tyr | Thr | Ser | Thr | Gln | Tyr | Thr |      |
|     | 310 |     |     |     |     | 315 |     |     |     |     | 320 |     |     |     |     |      |

| aaa | ggg | ggc | cta | att | tac | aag | cta | act | gaa | gaa | aat | ctt | caa | tat | gtg | 1064 |
|-----|-----|-----|-----|-----|-----|-----|-----|-----|-----|-----|-----|-----|-----|-----|-----|------|
| Lys | Gly | Gly | Leu | Ile | Tyr | Lys | Leu | Thr | Glu | Glu | Asn | Leu | Gln | Tyr | Val |      |
| 325 |     |     |     |     | 330 |     |     |     |     | 335 |     |     |     |     | 340 |      |

| aca | tcc | atc | aca | tct | ttg | ctc | acc | act | tat | gcc | aaa | tat | atg | gct | agt | 1112 |
|-----|-----|-----|-----|-----|-----|-----|-----|-----|-----|-----|-----|-----|-----|-----|-----|------|
| Thr | Ser | Ile | Thr | Ser | Leu | Leu | Thr | Thr | Tyr | Ala | Lys | Tyr | Met | Ala | Ser |      |
|     |     |     |     | 345 |     |     |     |     | 350 |     |     |     |     | 355 |     |      |

| aaa | aag | cat | act | ttc | aac | tgt | gga | agc | ctc | ttg | gtc | aca | gaa | aag | acc | 1160 |
|-----|-----|-----|-----|-----|-----|-----|-----|-----|-----|-----|-----|-----|-----|-----|-----|------|
| Lys | Lys | His | Thr | Phe | Asn | Cys | Gly | Ser | Leu | Leu | Val | Thr | Glu | Lys | Thr |      |
|     |     |     | 360 |     |     |     |     | 365 |     |     |     |     | 370 |     |     |      |

| att | aga | ata | ctt | gca | aaa | aga | cag | gtg | gac | tat | ata | ttg | ggt | aac | aat | 1208 |
|-----|-----|-----|-----|-----|-----|-----|-----|-----|-----|-----|-----|-----|-----|-----|-----|------|
| Ile | Arg | Ile | Leu | Ala | Lys | Arg | Gln | Val | Asp | Tyr | Ile | Leu | Gly | Asn | Asn |      |
|     |     | 375 |     |     |     |     | 380 |     |     |     |     | 385 |     |     |     |      |

```
cca atg aaa atg tca tac atg gta ggc tat gga aca aat tac cct cga      1256
Pro Met Lys Met Ser Tyr Met Val Gly Tyr Gly Thr Asn Tyr Pro Arg
    390                 395                 400 aga gtt cac cac aga gga tca tct tta cct tca atg gca atg cat cca      1304
Arg Val His His Arg Gly Ser Ser Leu Pro Ser Met Ala Met His Pro
405                 410                 415                 420 cag tca ttt ggt tgt gat ggt gga ttt caa cca tac tat tat aca gca      1352
Gln Ser Phe Gly Cys Asp Gly Gly Phe Gln Pro Tyr Tyr Tyr Thr Ala
                425                 430                 435 aat gcc aac cca aac ata ttg gtt gga gca att gtt gga ggt cct aat      1400
Asn Ala Asn Pro Asn Ile Leu Val Gly Ala Ile Val Gly Gly Pro Asn
                    440                 445                 450 caa aat gat ttc ttc ccg gat gaa cgt aca gat tat agt cat tca gag      1448
Gln Asn Asp Phe Phe Pro Asp Glu Arg Thr Asp Tyr Ser His Ser Glu
                455                 460                 465 cct gct act tat att aat gct gcc att gtt gga cct cta gca tac ttt      1496
Pro Ala Thr Tyr Ile Asn Ala Ala Ile Val Gly Pro Leu Ala Tyr Phe
470                 475                 480 gat agt tcc gaa cgt tag ggaaaattaa aagaggtata agggggttgtt            1544
Asp Ser Ser Glu Arg
485 ttactttttaa aatttgtaaa tatatcccta gattgttgtc caaaaacata tgggcatgtg   1604
cccccaaaag ttggtggcta cgtagggata cttttaatat acccttctca tgtaccctgt    1664
tttagatgtt cttttgtttt tagttgggtt gttttcttaa agtggatggt ttaaaatttt    1723

<210> SEQ ID NO 4
<211> LENGTH: 489
<212> TYPE: PRT
<213> ORGANISM: Nicotiana tabacum

<400> SEQUENCE: 4

Met Ala Phe Arg Val Glu Val Ser Val Cys Ile Ile Leu Phe Ser Ser
1               5                   10                  15

Phe Phe Phe Ser Leu Gly Thr Ala Gln Gly Val Phe Asn Tyr Arg Glu
                20                  25                  30

Ala Leu Glu Lys Ser Ile Leu Phe Phe Glu Gly Gln Arg Ser Gly Lys
            35                  40                  45

Leu Pro His Asn Gln Arg Val Ser Trp Arg Gly Ser Ser Gly Leu Ser
        50                  55                  60

Asp Gly Ser Leu Ala Lys Val Asp Leu Thr Gly Gly Tyr Tyr Asp Ala
65                  70                  75                  80

Gly Asp Asn Val Lys Phe Asn Phe Pro Met Ala Tyr Thr Thr Thr Leu
                85                  90                  95

Leu Ser Trp Asn Thr Leu Glu Tyr Gly Lys Arg Met Gly Pro Gln Leu
            100                 105                 110

Gln Asn Ala Arg Ala Ala Ile Arg Trp Ala Thr Asp Tyr Leu Leu Lys
        115                 120                 125

Cys Ala Asn Ala Ala Pro Asn Lys Leu Phe Val Gly Val Gly Asp Pro
130                 135                 140

Asn Ser Asp His Lys Cys Trp Glu Arg Pro Glu Asp Met Asp Thr Val
145                 150                 155                 160

Arg Ser Val Tyr Tyr Val Ser Pro Ser Pro Gly Ser Asp Val Ala
                165                 170                 175

Gly Glu Met Ala Ala Ala Leu Ala Ala Ala Ser Leu Val Phe Arg Thr
            180                 185                 190

Val Asp Pro Val Tyr Ser Lys Lys Leu Leu Gly Asn Ala Val Lys Val
```

-continued

```
                195                 200                 205
Phe Arg Phe Ala Val Gln Tyr Arg Gly Ser Tyr Ser Asp Ser Leu Gly
    210                 215                 220

Ser Ala Ala Cys Pro Phe Tyr Cys Ser Tyr Ser Gly Tyr Lys Asp Glu
225                 230                 235                 240

Leu Tyr Trp Gly Ala Ala Trp Leu Leu Arg Ala Thr Asn Asp Ile Ser
                245                 250                 255

Tyr Leu Asn Phe Ile Asn Thr Leu Gly Ala Asn Asp Val Pro Asp Leu
            260                 265                 270

Phe Ser Trp Asp Asn Lys Tyr Ala Gly His Val Leu Met Ala Arg
        275                 280                 285

Arg Ser Val Val Gly Asn Asp Lys Arg Phe Asp Pro Phe Arg Gln Gln
    290                 295                 300

Ala Glu Asp Phe Val Cys Lys Ile Leu Pro Asn Ser Pro Tyr Thr Ser
305                 310                 315                 320

Thr Gln Tyr Thr Lys Gly Gly Leu Ile Tyr Lys Leu Thr Glu Glu Asn
                325                 330                 335

Leu Gln Tyr Val Thr Ser Ile Thr Ser Leu Leu Thr Thr Tyr Ala Lys
            340                 345                 350

Tyr Met Ala Ser Lys Lys His Thr Phe Asn Cys Gly Ser Leu Leu Val
        355                 360                 365

Thr Glu Lys Thr Ile Arg Ile Leu Ala Lys Arg Gln Val Asp Tyr Ile
    370                 375                 380

Leu Gly Asn Asn Pro Met Lys Met Ser Tyr Met Val Gly Tyr Gly Thr
385                 390                 395                 400

Asn Tyr Pro Arg Arg Val His His Arg Gly Ser Ser Leu Pro Ser Met
                405                 410                 415

Ala Met His Pro Gln Ser Phe Gly Cys Asp Gly Gly Phe Gln Pro Tyr
            420                 425                 430

Tyr Tyr Thr Ala Asn Ala Asn Pro Asn Ile Leu Val Gly Ala Ile Val
        435                 440                 445

Gly Gly Pro Asn Gln Asn Asp Phe Phe Pro Asp Glu Arg Thr Asp Tyr
    450                 455                 460

Ser His Ser Glu Pro Ala Thr Tyr Ile Asn Ala Ala Ile Val Gly Pro
465                 470                 475                 480

Leu Ala Tyr Phe Asp Ser Ser Glu Arg
                485
```

<210> SEQ ID NO 5
<211> LENGTH: 2286
<212> TYPE: DNA
<213> ORGANISM: Nicotiana tabacum
<220> FEATURE:
<221> NAME/KEY: CDS
<222> LOCATION: (29)..(1903)
<223> OTHER INFORMATION:

<400> SEQUENCE: 5

```
gatctacaca gttgagattt ctaagcat atg atg aaa agt ttt gtc atg atg    52
                             Met Met Lys Ser Phe Val Met Met
                               1               5 ttt tgt tcc atg act cct ctg ctt ctt ata att ggg cta ctt cct aat  100
Phe Cys Ser Met Thr Pro Leu Leu Leu Ile Ile Gly Leu Leu Pro Asn
    10                  15                  20 ttg gca ttt gct agt agc cat aat tat ggt gaa gca ctt agc aaa agc  148
Leu Ala Phe Ala Ser Ser His Asn Tyr Gly Glu Ala Leu Ser Lys Ser
25                  30                  35                  40
```

| | | | | | | | | | | | | | | | | |
|---|---|---|---|---|---|---|---|---|---|---|---|---|---|---|---|---|
| ttt | ctg | ttt | tac | gag | gct | cag | aga | tct | ggt | tat | ctt | cct | cat | gac | cag | 196 |
| Phe | Leu | Phe | Tyr | Glu | Ala | Gln | Arg | Ser | Gly | Tyr | Leu | Pro | His | Asp | Gln | |
| | | | | 45 | | | | | 50 | | | | | 55 | | |
| aga | gtt | caa | tgg | agg | ggt | aat | tct | ggt | ctt | ctt | gac | ggc | aag | gct | agt | 244 |
| Arg | Val | Gln | Trp | Arg | Gly | Asn | Ser | Gly | Leu | Leu | Asp | Gly | Lys | Ala | Ser | |
| | | 60 | | | | | 65 | | | | | 70 | | | | |
| ggg | gtg | gat | cta | gta | gga | ggg | tac | tac | gat | gca | ggg | gat | aat | gtg | aaa | 292 |
| Gly | Val | Asp | Leu | Val | Gly | Gly | Tyr | Tyr | Asp | Ala | Gly | Asp | Asn | Val | Lys | |
| | | | 75 | | | | | 80 | | | | | 85 | | | |
| ttt | gga | ctg | cca | atg | gca | ttc | acc | gtt | aca | atg | atg | tcg | tgg | agc | atc | 340 |
| Phe | Gly | Leu | Pro | Met | Ala | Phe | Thr | Val | Thr | Met | Met | Ser | Trp | Ser | Ile | |
| | 90 | | | | | 95 | | | | | 100 | | | | | |
| ata | gaa | tat | ggg | aag | caa | atg | ggt | gaa | agt | gga | gag | ctt | agc | aat | gcc | 388 |
| Ile | Glu | Tyr | Gly | Lys | Gln | Met | Gly | Glu | Ser | Gly | Glu | Leu | Ser | Asn | Ala | |
| 105 | | | | | 110 | | | | | 115 | | | | | 120 | |
| ata | gat | gct | gtt | aaa | tgg | ggt | act | gat | tac | ctt | ctt | aaa | gct | cac | cct | 436 |
| Ile | Asp | Ala | Val | Lys | Trp | Gly | Thr | Asp | Tyr | Leu | Leu | Lys | Ala | His | Pro | |
| | | | | 125 | | | | | 130 | | | | | 135 | | |
| gaa | cca | aat | gtc | ctt | tat | gga | gag | gtt | gga | gat | ggt | acg | aca | gac | cat | 484 |
| Glu | Pro | Asn | Val | Leu | Tyr | Gly | Glu | Val | Gly | Asp | Gly | Thr | Thr | Asp | His | |
| | | | 140 | | | | | 145 | | | | | 150 | | | |
| tac | tgt | tgg | caa | aga | cca | gag | gac | atg | act | act | tca | aga | gct | gct | tac | 532 |
| Tyr | Cys | Trp | Gln | Arg | Pro | Glu | Asp | Met | Thr | Thr | Ser | Arg | Ala | Ala | Tyr | |
| | | | 155 | | | | | 160 | | | | | 165 | | | |
| agg | atc | gat | cca | agt | cgc | cct | gga | tcc | gat | ctc | gct | ggc | gag | aca | gct | 580 |
| Arg | Ile | Asp | Pro | Ser | Arg | Pro | Gly | Ser | Asp | Leu | Ala | Gly | Glu | Thr | Ala | |
| | 170 | | | | | 175 | | | | | 180 | | | | | |
| gcc | gca | atg | gca | gct | gct | tcc | atc | gtc | ttt | cgg | aac | agc | aac | cct | gct | 628 |
| Ala | Ala | Met | Ala | Ala | Ala | Ser | Ile | Val | Phe | Arg | Asn | Ser | Asn | Pro | Ala | |
| 185 | | | | | 190 | | | | | 195 | | | | | 200 | |
| tat | gcc | aaa | gag | ctc | ctc | act | cat | gcc | tac | cag | cta | ttc | gag | ttt | gcg | 676 |
| Tyr | Ala | Lys | Glu | Leu | Leu | Thr | His | Ala | Tyr | Gln | Leu | Phe | Glu | Phe | Ala | |
| | | | | 205 | | | | | 210 | | | | | 215 | | |
| gac | aaa | tac | agg | ggc | aaa | tat | gat | agc | agc | att | act | gtg | gcc | cag | aag | 724 |
| Asp | Lys | Tyr | Arg | Gly | Lys | Tyr | Asp | Ser | Ser | Ile | Thr | Val | Ala | Gln | Lys | |
| | | | 220 | | | | | 225 | | | | | 230 | | | |
| tac | tac | cga | tct | gtc | agt | gga | tac | gca | gat | gaa | tta | ctg | tgg | gcc | gcg | 772 |
| Tyr | Tyr | Arg | Ser | Val | Ser | Gly | Tyr | Ala | Asp | Glu | Leu | Leu | Trp | Ala | Ala | |
| | | | 235 | | | | | 240 | | | | | 245 | | | |
| gca | tgg | ctg | tac | aag | gca | tcc | aac | aaa | gaa | tat | tac | ttg | aac | tac | cta | 820 |
| Ala | Trp | Leu | Tyr | Lys | Ala | Ser | Asn | Lys | Glu | Tyr | Tyr | Leu | Asn | Tyr | Leu | |
| | 250 | | | | | 255 | | | | | 260 | | | | | |
| ggg | gag | aat | ggg | gat | gca | ctt | ggt | gga | act | ggt | tgg | tcc | atg | act | gaa | 868 |
| Gly | Glu | Asn | Gly | Asp | Ala | Leu | Gly | Gly | Thr | Gly | Trp | Ser | Met | Thr | Glu | |
| 265 | | | | | 270 | | | | | 275 | | | | | 280 | |
| ttt | ggc | tgg | gat | gtc | aag | tat | gct | ggt | gtc | cag | act | ctt | gct | gct | aag | 916 |
| Phe | Gly | Trp | Asp | Val | Lys | Tyr | Ala | Gly | Val | Gln | Thr | Leu | Ala | Ala | Lys | |
| | | | | 285 | | | | | 290 | | | | | 295 | | |
| ttc | cta | atg | caa | ggg | aat | gct | ggt | aac | cat | gca | cct | gtg | ttt | gag | aag | 964 |
| Phe | Leu | Met | Gln | Gly | Asn | Ala | Gly | Asn | His | Ala | Pro | Val | Phe | Glu | Lys | |
| | | | 300 | | | | | 305 | | | | | 310 | | | |
| tac | caa | gaa | aag | gct | gag | aat | ttt | atg | tgt | gca | tgt | ctt | ggg | aag | ggt | 1012 |
| Tyr | Gln | Glu | Lys | Ala | Glu | Asn | Phe | Met | Cys | Ala | Cys | Leu | Gly | Lys | Gly | |
| | | | 315 | | | | | 320 | | | | | 325 | | | |
| aac | caa | aac | atc | cac | aag | agt | cca | gga | ggt | ctc | att | ttc | cgc | cag | aga | 1060 |
| Asn | Gln | Asn | Ile | His | Lys | Ser | Pro | Gly | Gly | Leu | Ile | Phe | Arg | Gln | Arg | |
| | | 330 | | | | | 335 | | | | | 340 | | | | |
| tgg | aac | aat | atg | caa | ttt | gtc | aca | agt | gct | tct | ttc | ctt | gcc | act | gtc | 1108 |
| Trp | Asn | Asn | Met | Gln | Phe | Val | Thr | Ser | Ala | Ser | Phe | Leu | Ala | Thr | Val | |

-continued

| | | | |
|---|---|---|---|
| tac tct gac tat tta gcc tct gct aga aaa tcc ctc aag tgt tca tct<br>Tyr Ser Asp Tyr Leu Ala Ser Ala Arg Lys Ser Leu Lys Cys Ser Ser<br>345                350                355              360 | 1156 |

```
tac tct gac tat tta gcc tct gct aga aaa tcc ctc aag tgt tca tct      1156
Tyr Ser Asp Tyr Leu Ala Ser Ala Arg Lys Ser Leu Lys Cys Ser Ser
            365                 370                 375 ggc act gta tta cca tct gag ctc ctc tca ttt gcc aag tca cag gtt      1204
Gly Thr Val Leu Pro Ser Glu Leu Leu Ser Phe Ala Lys Ser Gln Val
            380                 385                 390 gac tac att ctt gga gat aac cca aga gcc aca agt tac atg gtg gga      1252
Asp Tyr Ile Leu Gly Asp Asn Pro Arg Ala Thr Ser Tyr Met Val Gly
        395                 400                 405 tat gga aac aac tac cca aga caa gtt cac cac aga ggt tct tcc att      1300
Tyr Gly Asn Asn Tyr Pro Arg Gln Val His His Arg Gly Ser Ser Ile
    410                 415                 420 gtt tct gta aag aag gat cct tct ttt gtt agc tgc cgt gga ggt tat      1348
Val Ser Val Lys Lys Asp Pro Ser Phe Val Ser Cys Arg Gly Gly Tyr
425                 430                 435                 440 gcc act tgg ttt agt aga aag gcg agt gat ccc aat ctt cta gct gga      1396
Ala Thr Trp Phe Ser Arg Lys Ala Ser Asp Pro Asn Leu Leu Ala Gly
                445                 450                 455 gcc att gtt ggt gga cct gat gcc tat gac aac ttt gct gat cag agg      1444
Ala Ile Val Gly Gly Pro Asp Ala Tyr Asp Asn Phe Ala Asp Gln Arg
            460                 465                 470 gac aac tat gag caa act gaa cca gcc acc tac aac aat gct cct ttg      1492
Asp Asn Tyr Glu Gln Thr Glu Pro Ala Thr Tyr Asn Asn Ala Pro Leu
        475                 480                 485 att ggt gtg tta gca aga ctt cat ggt ggt caa agt aaa tat agt cag      1540
Ile Gly Val Leu Ala Arg Leu His Gly Gly Gln Ser Lys Tyr Ser Gln
    490                 495                 500 ctc ctt cca gtt gct atc cct cag cca aag cca gat cca gag caa aaa      1588
Leu Leu Pro Val Ala Ile Pro Gln Pro Lys Pro Asp Pro Glu Gln Lys
505                 510                 515                 520 gta act cca gcc cca gct tca tca act gct gac att act att gaa caa      1636
Val Thr Pro Ala Pro Ala Ser Ser Thr Ala Asp Ile Thr Ile Glu Gln
                525                 530                 535 aag gaa aca gct tca tgg gtt ccc aag ggg aaa act tac tac aga tac      1684
Lys Glu Thr Ala Ser Trp Val Pro Lys Gly Lys Thr Tyr Tyr Arg Tyr
            540                 545                 550 tca gta ata gta act aac aaa tct gct atg aca atg aag aat ttg aaa      1732
Ser Val Ile Val Thr Asn Lys Ser Ala Met Thr Met Lys Asn Leu Lys
        555                 560                 565 ctc tca ata tac caa ctc tat ggt tct ctc tgg ggt ctt tca aaa tat      1780
Leu Ser Ile Tyr Gln Leu Tyr Gly Ser Leu Trp Gly Leu Ser Lys Tyr
    570                 575                 580 ggt gac tcc tac gta ttc ccg gcc tgg ctc aac tct tta cca gct gga      1828
Gly Asp Ser Tyr Val Phe Pro Ala Trp Leu Asn Ser Leu Pro Ala Gly
585                 590                 595                 600 aaa acc ctc gag ttt gtg tac gtt cac tct gct tct cct gca acg gtc      1876
Lys Thr Leu Glu Phe Val Tyr Val His Ser Ala Ser Pro Ala Thr Val
                605                 610                 615 tcc ata tca agc tac act ctt gtc taa aacccaaaag acgacgtgaa            1923
Ser Ile Ser Ser Tyr Thr Leu Val
                620 tctacaaaga atgaatcatc aactctgggg ttttaatgta agaattgtgc agttgtttgt    1983 aacttttcaa cttcttggtt tgtagtttga gttattaggt gtttagctat tgaagtgtag    2043 gttaaataaa ggcggatatc tggaggaaga aaggagcgaa gagacgaatt agaacaagtg    2103 ctcatcctct ttcttctcca cttcattttg tcacattata gcatagtatt gagaaaagag    2163 tgaggggctg agaaattaag aaggttgctt ctcaacagaa atgtgaagtt gatcttcatt    2223
```

```
ttgtaattta tgcaatttca aggttttcat atgttaaaaa aaaaaaaaaa aaaaaaaaa    2283 aaa                                                                2286
```

<210> SEQ ID NO 6
<211> LENGTH: 624
<212> TYPE: PRT
<213> ORGANISM: Nicotiana tabacum

<400> SEQUENCE: 6

```
Met Met Lys Ser Phe Val Met Met Phe Cys Ser Met Thr Pro Leu Leu
1               5                   10                  15

Leu Ile Ile Gly Leu Leu Pro Asn Leu Ala Phe Ala Ser Ser His Asn
            20                  25                  30

Tyr Gly Glu Ala Leu Ser Lys Ser Phe Leu Phe Tyr Glu Ala Gln Arg
        35                  40                  45

Ser Gly Tyr Leu Pro His Asp Gln Arg Val Gln Trp Arg Gly Asn Ser
    50                  55                  60

Gly Leu Leu Asp Gly Lys Ala Ser Gly Val Asp Leu Val Gly Gly Tyr
65                  70                  75                  80

Tyr Asp Ala Gly Asp Asn Val Lys Phe Gly Leu Pro Met Ala Phe Thr
                85                  90                  95

Val Thr Met Met Ser Trp Ser Ile Ile Glu Tyr Gly Lys Gln Met Gly
            100                 105                 110

Glu Ser Gly Glu Leu Ser Asn Ala Ile Asp Ala Val Lys Trp Gly Thr
        115                 120                 125

Asp Tyr Leu Leu Lys Ala His Pro Glu Pro Asn Val Leu Tyr Gly Glu
    130                 135                 140

Val Gly Asp Gly Thr Thr Asp His Tyr Cys Trp Gln Arg Pro Glu Asp
145                 150                 155                 160

Met Thr Thr Ser Arg Ala Ala Tyr Arg Ile Asp Pro Ser Arg Pro Gly
                165                 170                 175

Ser Asp Leu Ala Gly Glu Thr Ala Ala Met Ala Ala Ala Ser Ile
            180                 185                 190

Val Phe Arg Asn Ser Asn Pro Ala Tyr Ala Lys Glu Leu Leu Thr His
        195                 200                 205

Ala Tyr Gln Leu Phe Glu Phe Ala Asp Lys Tyr Arg Gly Lys Tyr Asp
    210                 215                 220

Ser Ser Ile Thr Val Ala Gln Lys Tyr Tyr Arg Ser Val Ser Gly Tyr
225                 230                 235                 240

Ala Asp Glu Leu Leu Trp Ala Ala Ala Trp Leu Tyr Lys Ala Ser Asn
                245                 250                 255

Lys Glu Tyr Tyr Leu Asn Tyr Leu Gly Glu Asn Gly Asp Ala Leu Gly
            260                 265                 270

Gly Thr Gly Trp Ser Met Thr Glu Phe Gly Trp Asp Val Lys Tyr Ala
        275                 280                 285

Gly Val Gln Thr Leu Ala Ala Lys Phe Leu Met Gln Gly Asn Ala Gly
    290                 295                 300

Asn His Ala Pro Val Phe Glu Lys Tyr Gln Glu Lys Ala Glu Asn Phe
305                 310                 315                 320

Met Cys Ala Cys Leu Gly Lys Gly Asn Gln Asn Ile His Lys Ser Pro
                325                 330                 335

Gly Gly Leu Ile Phe Arg Gln Arg Trp Asn Asn Met Gln Phe Val Thr
            340                 345                 350
```

```
Ser Ala Ser Phe Leu Ala Thr Val Tyr Ser Asp Tyr Leu Ala Ser Ala
        355                 360                 365

Arg Lys Ser Leu Lys Cys Ser Ser Gly Thr Val Leu Pro Ser Glu Leu
    370                 375                 380

Leu Ser Phe Ala Lys Ser Gln Val Asp Tyr Ile Leu Gly Asp Asn Pro
385                 390                 395                 400

Arg Ala Thr Ser Tyr Met Val Gly Tyr Gly Asn Asn Tyr Pro Arg Gln
                405                 410                 415

Val His His Arg Gly Ser Ser Ile Val Ser Val Lys Lys Asp Pro Ser
                420                 425                 430

Phe Val Ser Cys Arg Gly Gly Tyr Ala Thr Trp Phe Ser Arg Lys Ala
            435                 440                 445

Ser Asp Pro Asn Leu Leu Ala Gly Ala Ile Val Gly Gly Pro Asp Ala
        450                 455                 460

Tyr Asp Asn Phe Ala Asp Gln Arg Asp Asn Tyr Glu Gln Thr Glu Pro
465                 470                 475                 480

Ala Thr Tyr Asn Asn Ala Pro Leu Ile Gly Val Leu Ala Arg Leu His
                485                 490                 495

Gly Gly Gln Ser Lys Tyr Ser Gln Leu Leu Pro Val Ala Ile Pro Gln
            500                 505                 510

Pro Lys Pro Asp Pro Glu Gln Lys Val Thr Pro Ala Pro Ala Ser Ser
        515                 520                 525

Thr Ala Asp Ile Thr Ile Glu Gln Lys Glu Thr Ala Ser Trp Val Pro
        530                 535                 540

Lys Gly Lys Thr Tyr Tyr Arg Tyr Ser Val Ile Val Thr Asn Lys Ser
545                 550                 555                 560

Ala Met Thr Met Lys Asn Leu Lys Leu Ser Ile Tyr Gln Leu Tyr Gly
                565                 570                 575

Ser Leu Trp Gly Leu Ser Lys Tyr Gly Asp Ser Tyr Val Phe Pro Ala
            580                 585                 590

Trp Leu Asn Ser Leu Pro Ala Gly Lys Thr Leu Glu Phe Val Tyr Val
        595                 600                 605

His Ser Ala Ser Pro Ala Thr Val Ser Ile Ser Ser Tyr Thr Leu Val
        610                 615                 620

<210> SEQ ID NO 7
<211> LENGTH: 8
<212> TYPE: PRT
<213> ORGANISM: Artificial Sequence
<220> FEATURE:
<223> OTHER INFORMATION: Conserved amino acid domain of plant EGases.

<400> SEQUENCE: 7

Cys Trp Glu Arg Pro Glu Asp Met
1               5

<210> SEQ ID NO 8
<211> LENGTH: 6
<212> TYPE: PRT
<213> ORGANISM: Artificial Sequence
<220> FEATURE:
<223> OTHER INFORMATION: Conserved amino acid domain of plant EGases

<400> SEQUENCE: 8

Tyr Ile Asn Ala Pro Leu
1               5

<210> SEQ ID NO 9
```

<211> LENGTH: 1470
<212> TYPE: DNA
<213> ORGANISM: Nicotiana tabacum

<400> SEQUENCE: 9

| | | | | | | |
|---|---|---|---|---|---|---|
| atgcccattc | atcaagaatc | tagatcatga | agtgcataac | tatttatgct | aaggagtgga | 60 |
| ctaaaagtta | ttgtcaatta | tattgacaca | tgttttgtat | caatgtaaaa | ataggagtt | 120 |
| tgcagaaatt | ccattattat | aggcaggttg | catatgcttt | tgatcattta | ctatctcggc | 180 |
| tttcaacatt | cacctaataa | acacatgagg | aatacgaatg | tgcaattagc | ttaagttggg | 240 |
| aaagaaaaca | tgaagcatta | cgccgtaggc | ctaaaggact | gatagcttat | ccattttct | 300 |
| tttctttcat | tctcgtcttt | ccgatataca | atgacaacct | acatgttctt | tgtactgtca | 360 |
| gcttaattta | acatgtgata | ttaagttaat | tacgtataat | tattattaaa | attaattttt | 420 |
| agatttagtg | acttgattgt | gttaataatt | tttaaactgt | cagtgaatat | atcttttaaa | 480 |
| ttcattagta | aacttgctaa | tccttaaata | aaaatataa | aaaggccatt | gaaaatcaa | 540 |
| atggtagaat | acttctctga | tttaataaat | atatgggaaa | agaagtaatt | aaaaagagtc | 600 |
| tattaatctt | caacaccaca | agtcagataa | agatgtcact | ctgcagtaga | gggtaaatat | 660 |
| cacatcgcat | tggtactcca | aaaagagga | gggaaaagaa | aggtgatcgt | tttggccttc | 720 |
| ccatttatag | ggattcgaga | cggccaaatg | tgaatttaca | agagttaatt | tcctcgaatg | 780 |
| ccatgatagc | cttatagaag | ttagtagttg | tgaagaaaac | tcaaagatat | ttggtgagat | 840 |
| gcaagtggaa | atatcggatt | taacatttaa | gcgtatacaa | atactgatag | tgaaaacttt | 900 |
| ttacatcatc | actatagttt | aaattatata | gcaaatcacg | tactatttat | tgtaggttat | 960 |
| gaattaatat | ttattaaata | aaattatttg | taattatctt | ttaaatgatt | tgattgtata | 1020 |
| aatatttctt | atatcataag | tgcatatatt | taaagctcga | acatatttct | aaagtattt | 1080 |
| tgggagtcat | gtgttttccc | tccattccat | tttctctata | gtcttcaaac | actttgattt | 1140 |
| gcttttagtc | ttttgttcac | tcatctcgaa | attcttggtc | aacctaaact | agttctaaga | 1200 |
| gattagaagc | cgctaccttt | aggcatggac | taccttttcg | tgtatttcga | tagagtacat | 1260 |
| gtttactcaa | atggaaatta | aattaaatat | ttttctaaa | gggaatgaca | ataaagaaaa | 1320 |
| agacacttga | ttggaaagcc | ttaatttgcg | ttgctgtgat | tggattcccc | aagcccctat | 1380 |
| ataagggt | catttgtcaa | tgttttaatc | aacgccataa | ctaactctaa | ataagccatt | 1440 |
| ttatactttg | agcaaatcaa | aaaaagtata | | | | 1470 |

<210> SEQ ID NO 10
<211> LENGTH: 21
<212> TYPE: DNA
<213> ORGANISM: Artificial Sequence
<220> FEATURE:
<223> OTHER INFORMATION: Degenerate oligonucleotide primer.

<400> SEQUENCE: 10
tgttgggara grcchgarga y                                              21

<210> SEQ ID NO 11
<211> LENGTH: 24
<212> TYPE: DNA
<213> ORGANISM: Artificial Sequence
<220> FEATURE:
<223> OTHER INFORMATION: Degenerate oligonucleotide primer.

<400> SEQUENCE: 11
machadhgsw gcattrayrt awgt                                           24

```
<210> SEQ ID NO 12
<211> LENGTH: 38
<212> TYPE: DNA
<213> ORGANISM: Artificial Sequence
<220> FEATURE:
<223> OTHER INFORMATION: Degenerate oligonucleotide primer.

<400> SEQUENCE: 12
cgcggatccg grttrtywcc harhawrtar tchacytg                              38

<210> SEQ ID NO 13
<211> LENGTH: 32
<212> TYPE: DNA
<213> ORGANISM: Artificial Sequence
<220> FEATURE:
<223> OTHER INFORMATION: 5' tobcel2-specific synthetic oligonucleotide
      primer.

<400> SEQUENCE: 13
ccggaattcg taacatgcag catgtgacat cc                                    32

<210> SEQ ID NO 14
<211> LENGTH: 31
<212> TYPE: DNA
<213> ORGANISM: Artificial Sequence
<220> FEATURE:
<223> OTHER INFORMATION: 5' tobcel4-specific synthetic oligonucleotide
      primer.

<400> SEQUENCE: 14
ccggaattcg catgttggag caaggatctt c                                     31

<210> SEQ ID NO 15
<211> LENGTH: 32
<212> TYPE: DNA
<213> ORGANISM: Artificial Sequence
<220> FEATURE:
<223> OTHER INFORMATION: 5' tobcel5-specific synthetic oligonucleotide
      primer.

<400> SEQUENCE: 15
ccggaattcc caggctcacc tagctttcaa gc                                    32

<210> SEQ ID NO 16
<211> LENGTH: 32
<212> TYPE: DNA
<213> ORGANISM: Artificial Sequence
<220> FEATURE:
<223> OTHER INFORMATION: 5' tobcel7-specific synthetic oligonucleotide
      primer.

<400> SEQUENCE: 16
ccggaattcg ggggcctaat ttacaagcta ac                                    32

<210> SEQ ID NO 17
<211> LENGTH: 34
<212> TYPE: DNA
<213> ORGANISM: Artificial Sequence
<220> FEATURE:
<223> OTHER INFORMATION: 5' tobcel8-specific synthetic oligonucleotide
      primer.

<400> SEQUENCE: 17
ccggaattcc catgcacctg tgtttgagaa gtac                                  34
```

-continued

```
<210> SEQ ID NO 18
<211> LENGTH: 31
<212> TYPE: DNA
<213> ORGANISM: Artificial Sequence
<220> FEATURE:
<223> OTHER INFORMATION: 5' tobcel8-2 gene-specific synthetic
      oligonucleotide primer.

<400> SEQUENCE: 18
ccggaattcc gtctttcgga acagcaaccc t                              31

<210> SEQ ID NO 19
<211> LENGTH: 32
<212> TYPE: DNA
<213> ORGANISM: Artificial Sequence
<220> FEATURE:
<223> OTHER INFORMATION: 3' tobcel8-2 gene-specific synthetic
      oligonucleotide primer.

<400> SEQUENCE: 19
cgcggatcct tcatctgcgt atccactgac ag                             32

<210> SEQ ID NO 20
<211> LENGTH: 32
<212> TYPE: DNA
<213> ORGANISM: Artificial Sequence
<220> FEATURE:
<223> OTHER INFORMATION: Synthetic oligonucleotide primer to tobacco 18S
      ribosomal RNA.

<400> SEQUENCE: 20
ccggaattcg aatgatccgg tgaagtgttc gg                             32

<210> SEQ ID NO 21
<211> LENGTH: 33
<212> TYPE: DNA
<213> ORGANISM: Artificial Sequence
<220> FEATURE:
<223> OTHER INFORMATION: Synthetic oligonucleotide primer to tobacco 18S
      ribosomal RNA.

<400> SEQUENCE: 21
cgcggatccg ataaggttta gtggacttct cgc                            33
```